US012697342B2

(12) United States Patent
Ko et al.

(10) Patent No.: US 12,697,342 B2
(45) Date of Patent: Aug. 4, 2026

(54) NON-SURGICAL PREVENTION OF BOAR TAINT AND AGGRESSIVE BEHAVIOR

(71) Applicant: Insigna Inc., Champaign, IL (US)

(72) Inventors: CheMyong Ko, Champaign, IL (US); ChanJin Park, Savoy, IL (US); Po-Ching Patrick Lin, Champaign, IL (US); Rex Allen Hess, Champaign, IL (US); Suzanne Rene Broussard, Decatur, IL (US); Sherry Qi Zhou, Savoy, IL (US)

(73) Assignee: Insigna, Inc., Champaign, IL (US)

(*) Notice: Subject to any disclaimer, the term of this patent is extended or adjusted under 35 U.S.C. 154(b) by 127 days.

(21) Appl. No.: 18/437,978

(22) Filed: Feb. 9, 2024

(65) Prior Publication Data

US 2024/0180926 A1      Jun. 6, 2024

Related U.S. Application Data

(63) Continuation of application No. 17/937,740, filed on Oct. 3, 2022, now Pat. No. 11,938,140.

(60) Provisional application No. 63/365,389, filed on May 26, 2022.

(51) Int. Cl.

| | |
|---|---|
| *C07J 1/00* | (2006.01) |
| *A61K 9/00* | (2006.01) |
| *A61K 31/565* | (2006.01) |
| *A61K 31/568* | (2006.01) |
| *A61P 5/26* | (2006.01) |
| *A61P 5/30* | (2006.01) |
| *A61P 43/00* | (2006.01) |

(52) U.S. Cl.
CPC .......... *A61K 31/565* (2013.01); *A61K 9/0019* (2013.01); *A61K 9/0024* (2013.01); *A61K 9/0056* (2013.01); *A61K 31/568* (2013.01); *A61P 5/26* (2018.01); *A61P 5/30* (2018.01); *A61P 43/00* (2018.01)

(58) Field of Classification Search
CPC . C07J 1/00; A61K 9/00; A61K 31/565; A61K 31/568; A61P 5/26; A61P 5/30
See application file for complete search history.

(56) References Cited

U.S. PATENT DOCUMENTS

| | | | |
|---|---|---|---|
| 3,991,750 | A | 11/1976 | Vickery |
| 4,096,239 | A | 6/1978 | Katz et al. |
| 4,123,519 | A | 10/1978 | Tribble et al. |
| 4,210,644 | A | 7/1980 | Desjardins et al. |
| 4,610,687 | A | 9/1986 | Fogwell |
| 5,035,891 | A | 7/1991 | Runkel et al. |
| 5,314,882 | A | 5/1994 | Pantic et al. |
| 6,063,395 | A | 5/2000 | Markkula et al. |
| 6,458,387 | B1 | 10/2002 | Scott et al. |
| 7,589,082 | B2 | 9/2009 | Savoir et al. |
| 11,135,229 | B2 | 10/2021 | Ko |
| 11,938,140 | B2 | 3/2024 | Ko et al. |
| 2011/0112475 | A1 | 5/2011 | Benson |
| 2017/0258808 | A9 | 9/2017 | Yoakum et al. |
| 2020/0171047 | A1 | 6/2020 | Ko |
| 2020/0171048 | A1 | 6/2020 | Ko |
| 2022/0370474 | A1 | 11/2022 | Ko |
| 2023/0226075 | A1 | 7/2023 | Ko |
| 2023/0381197 | A1 | 11/2023 | Ko et al. |
| 2023/0381198 | A1 | 11/2023 | Ko et al. |
| 2023/0381199 | A1 | 11/2023 | Ko et al. |
| 2023/0381200 | A1 | 11/2023 | Ko et al. |
| 2026/0076978 | A1 | 3/2026 | Ko et al. |

FOREIGN PATENT DOCUMENTS

| | | |
|---|---|---|
| CN | 113423391 A | 9/2021 |
| EP | 3886816 B1 | 9/2023 |
| GB | 636908 A | 5/1950 |
| WO | WO-2020112180 A1 | 6/2020 |
| WO | WO-2023230607 A1 | 11/2023 |
| WO | WO-2023230619 A1 | 11/2023 |
| WO | WO-2023230621 A1 | 11/2023 |
| WO | WO-2024076995 A1 | 4/2024 |

OTHER PUBLICATIONS

"U.S. Appl. No. 16/526,874, 312 Amendment filed Jul. 8, 2021", 3 pgs.
"U.S. Appl. No. 16/526,874, Advisory Action mailed Sep. 9, 2020", 5 pgs.
"U.S. Appl. No. 16/526,874, Examiner Interview Summary mailed Jun. 1, 2021", 3 pgs.
"U.S. Appl. No. 16/526,874, Final Office Action mailed Apr. 26, 2021", 8 pgs.
"U.S. Appl. No. 16/526,874, Final Office Action mailed Jun. 9, 2020", 10 pgs.
"U.S. Appl. No. 16/526,874, Non Final Office Action mailed Nov. 24, 2020", 8 pgs.
"U.S. Appl. No. 16/526,874, Non Final Office Action mailed Dec. 11, 2019", 6 pgs.
"U.S. Appl. No. 16/526,874, Notice of Allowability mailed Aug. 30, 2021", 5 pgs.

(Continued)

*Primary Examiner* — Brenda L Coleman
(74) *Attorney, Agent, or Firm* — Schwegman Lundberg & Woessner, P.A.

(57) ABSTRACT

Embodiments of the present invention provide a pharmaceutical intervention in the neonatal pig that inhibits and delays development and activation of the HPG axis, growth of the boar testis and inhibits testicular production of testosterone and androstenone, which prevents the development of aggressive behavior in the maturing boars and the presence of boar taint in the meat. The invention comprises treatment with a combination of an androgen and an estrogen in the newborn male piglet using extended drug delivery methods, with a defined duration of no more than 12 weeks, for the purpose of inhibiting the production of testosterone and androstenone and the accumulation of the boar taint-inducing molecules androstenone and skatole in the fat.

19 Claims, 2 Drawing Sheets

(56)          References Cited

OTHER PUBLICATIONS

"U.S. Appl. No. 16/526,874, Notice of Allowance mailed Jul. 2, 2021", 8 pgs.

"U.S. Appl. No. 16/526,874, Response filed Feb. 16, 2021 to Non Final Office Action mailed Nov. 24, 2020", 7 pgs.

"U.S. Appl. No. 16/526,874, Response filed Mar. 10, 2020 to Non Final Office Action mailed Dec. 11, 2019", 7 pgs.

"U.S. Appl. No. 16/526,874, Response filed Jun. 9, 2021 to Final Office Action mailed Apr. 26, 2021", 7 pgs.

"U.S. Appl. No. 16/526,874, Response filed Aug. 17, 2020 to Final Office Action mailed Jun. 9, 2020", 8 pgs.

"U.S. Appl. No. 16/526,874, Response filed Oct. 9, 2020 to Advisory Action mailed Sep. 9, 2020", 10 pgs.

"U.S. Appl. No. 16/699,307, Final Office Action mailed Jan. 11, 2021", 12 pgs.

"U.S. Appl. No. 16/699,307, Non Final Office Action mailed May 12, 2020", 7 pgs.

"U.S. Appl. No. 16/699,307, Non Final Office Action mailed Jun. 28, 2021", 16 pgs.

"U.S. Appl. No. 16/699,307, Response filed Apr. 12, 2021 to Final Office Action mailed Jan. 11, 2021", 11 pgs.

"U.S. Appl. No. 16/699,307, Response filed Nov. 12, 2020 to Non Final Office Action mailed May 12, 2020", 8 pgs.

"U.S. Appl. No. 17/646,207, Final Office Action mailed Aug. 1, 2023", 11 pgs.

"U.S. Appl. No. 17/646,207, Non Final Office Action mailed Mar. 30, 2023", 9 pgs.

"U.S. Appl. No. 17/646,207, Preliminary Amendment filed Aug. 15, 2022", 5 pgs.

"U.S. Appl. No. 17/646,207, Response filed Jun. 29, 2023 to Non Final Office Action mailed Mar. 30, 2023", 11 pgs.

"U.S. Appl. No. 17/937,743, Advisory Action mailed Jan. 19, 2024", 3 pgs.

"U.S. Appl. No. 17/937,743, Non Final Office Action mailed Jul. 5, 2024", 25 pgs.

"U.S. Appl. No. 17/937,743, Response filed Jan. 3, 2024 to Final Office Action mailed Oct. 12, 2023", 7 pgs.

"U.S. Appl. No. 17/937,743, Response filed Dec. 5, 2024 to Non Final Office Action mailed Jul. 5, 2024", 9 pgs.

"U.S. Appl. No. 18/099,654, Preliminary Amendment filed Apr. 10, 2023", 9 pgs.

"Chinese Application Serial No. 201980089378.4, Decision of Rejection mailed Nov. 30, 2023", W/English Translation, 13 pgs.

"Chinese Application Serial No. 201980089378.4, Office Action mailed Apr. 12, 2023", w/English Translation, 11 pgs.

"Chinese Application Serial No. 201980089378.4, Office Action mailed Jul. 25, 2023", W/English Translation, 13 pgs.

"Chinese Application Serial No. 201980089378.4, Office Action mailed Aug. 29, 2022", w/English translation, 18 pgs.

"Chinese Application Serial No. 201980089378.4, Response Filed Jan. 13, 2023 to Office Action mailed Aug. 29, 2022", W/ English Claims, 13 pgs.

"Chinese Application Serial No. 201980089378.4, Response Filed Oct. 8, 2023 to Office Action mailed Jul. 25, 2023", W/ English Claims, 10 pgs.

"Chinese Application Serial No. 201980089378.4, Response Filed Jun. 27, 2023 to Office Action mailed Apr. 12, 2023", W/ English Claims, 7 pgs.

"European Application Serial No. 19891161.2, Extended European Search Report mailed Jul. 15, 2022", 9 pgs.

"European Application Serial No. 19891161.2, Response Filed Jan. 10, 2023 to Extended European Search Report mailed Jul. 15, 2022", 10 pgs.

"Guide to the care and use of experimental animals", Canadian Council on Animal Care, p. 371,Atomic Energy Press, vol. 1, (1993), 300 pgs.

"International Application Serial No. PCT/US2019/044230, International Preliminary Report on Patentability mailed Jun. 10, 2021", 6 pgs.

"International Application Serial No. PCT/US2019/044230, International Search Report mailed Oct. 29, 2019", 2 pgs.

"International Application Serial No. PCT/US2019/044230, Written Opinion mailed Oct. 29, 2019", 4 pgs.

"International Application Serial No. PCT/US2023/067550, International Preliminary Report on Patentability mailed Dec. 5, 2024", 6 pgs.

"International Application Serial No. PCT/US2023/067565, International Preliminary Report on Patentability mailed Dec. 5, 2024", 6 pgs.

"International Application Serial No. PCT/US2023/067568, International Preliminary Report on Patentability mailed Dec. 5, 2024", 6 pgs.

"International Application Serial No. PCT/US2023/075842, International Search Report mailed Mar. 15, 2024", 5 pgs.

"International Application Serial No. PCT/US2023/075842, Invitation to Pay Additional Fees mailed Jan. 23, 2024", 12 pgs.

"International Application Serial No. PCT/US2023/075842, Written Opinion mailed Mar. 15, 2024", 11 pgs.

"Korean Application Serial No. 10-2024-7042762, Notice of Preliminary Rejection mailed Dec. 27, 2024", w/ English Translation, 6 pgs.

"Korean Application Serial No. 10-2024-7042763, Office Action mailed Dec. 27, 2024", w/ English Translation, 6 pgs.

Babol, J., et al., "Relationship between metabolism of androstenone and skatole in intact male pigs", J Anim Sci, 77, (1999), 84-92.

Batrinos, M., et al., "Testosterone and aggressive behavior in man", Int J Endocrinol Metab, 10, (2012), 563-8.

Claus, R., et al., "Oestrogens, compared to other steroids of testicular origin, in blood plasma of boars", Acta Endocrinol (Copenh), 94, (1980), 404-411.

Giersing, M., et al., "Social effects and boar taint: significance for production of slaughter boars (Sus scrofa)", J Anim Sci, 78, (2000), 296-305.

Gorski, R A, "Modification of ovulatory mechanisms by postnatal administration of estrogen to the rat", American Journal of Physiology, vol. 205, No. 5, (1963), 842-844.

Griffiths, N. M., et al., "Human olfactory responses to 5-alpha-androst-16-en-3-one—principal component of boar taint", J Scl Food Agric, 21, (1970), 3 pgs.

Hayashi, S, "Sterilization of Female Rats by Neonatal Placement of Estradiol Micropellets in Anterior Hypothalamus", Endocrinol. Japan, vol. 23, No. 1, (1976), 55-60.

Kicman, A. T., "Pharmacology of anabolic steroids", British journal of pharmacology, 154, (2008), 502-521.

Kind, Fred A, et al., "Inhibition of sexual development in male and female rats treated with various steroids at the age of five days", Acta Endocrinogica vol. 49, No. 2, (Jun. 30, 1965), 193-206.

Lervik, S., et al., "Androstenone and testosterone levels and testicular morphology of Duroc boars related to estimated breeding value for androstenone", Theriogenology, 79, (2013), 986-994.

Lin-Schilstra, L., et al., "Paradoxical consumers in four European countries: Meat-eating justification and willingness to pay for meat from animals treated by alternatives to surgical castration", Meat Sci, 188: 108777, (2022), 12 pgs.

Llewellyn, W., et al., "Anabolics", Molecular Nutrition LLC, (2011), 1057 pgs.

Parois, S. P., et al., "Influence of the inflammatory status of entire male pigs on their pubertal development and fat androstenone", Animal, 11, (2017), 1071-1077.

Patterson, R. L. S., "5a-androst-16-ene-3-one:—Compound responsible for taint in boar fat.", Journal of the Science of Food and Agriculture, 19, (1968), 31-38.

Rebourcet, Diane, et al., "Sertoli Cells Maintain Leydig Cell Number and Peritubular Myoid Cell Activity in the Adult Mouse Testis", PLoS One, vol. 9, Issue 8, (2014), 13 pages.

Rosa-E-Silva, Alzira, et al., "Prepubertal Administration of Estradiol Valerate Disrupts Cyclicity and Leads to Cystic Ovarian Morphology during Adult Life in the Rat: Role of Sympathetic Innervation", Endocrinology, 144(10), (2003), 4289-4297.

U.S. Appl. No. 17/937,740, filed Oct. 3, 2022, Non-Surgical Prevention of Boar Taint and Aggressive Behavior.

(56)        References Cited

OTHER PUBLICATIONS

U.S. Appl. No. 17/937,743, filed Oct. 3, 2022, Compositions for Non-Surgical Prevention of Boar Taint and Aggressive Behavior.
U.S. Appl. No. 18/324,786, filed May 26, 2023, Prevention of Estrus in Sow and Ruminants.
U.S. Appl. No. 18/324,798, filed May 26, 2023, Non-Surgical Prevention of Unpleasant Odor in Meats and Aggressive or Sexual behavior in Male Ruminants.
"U.S. Appl. No. 17/937,740, 312 Amendment filed Dec. 12, 2023", 5 pgs.
"U.S. Appl. No. 17/937,740, Final Office Action mailed Oct. 30, 2023", 6 pgs.
"U.S. Appl. No. 17/937,740, Non Final Office Action mailed Jul. 28, 2023", 5 pgs.
"U.S. Appl. No. 17/937,740, Notice of Allowance mailed Dec. 6, 2023", 5 pgs.
"U.S. Appl. No. 17/937,740, PTO Response to Rule 312 Communication mailed Dec. 27, 2023", 2 pgs.
"U.S. Appl. No. 17/937,740, Response filed Oct. 13, 2023 to Non Final Office Action mailed Jul. 28, 2023", 5 pgs.
"U.S. Appl. No. 17/937,740, Response filed Nov. 17, 2023 to Final Office Action mailed Oct. 30, 2023", 4 pgs.
"U.S. Appl. No. 17/937,743, Final Office Action mailed Oct. 12, 2023", 17 pgs.
"U.S. Appl. No. 17/937,743, Non Final Office Action mailed Feb. 16, 2023".
"U.S. Appl. No. 17/937,743, Non Final Office Action mailed Jun. 8, 2023", 12 pgs.
"U.S. Appl. No. 17/937,743, Response filed Jan. 11, 2023 to Restriction Requirement mailed Jan. 5, 2023", 6 pgs.
"U.S. Appl. No. 17/937,743, Response filed May 16, 2023 to Non Final Office Action mailed Feb. 16, 2023", 6 pgs.
"U.S. Appl. No. 17/937,743, Response filed Sep. 8, 2023 to Non Final Office Action mailed Jun. 8, 2023", 10 pgs.
"U.S. Appl. No. 17/937,743, Restriction Requirement mailed Jan. 5, 2023".
"Claims of copending U.S. Appl. No. 17/937,740", (Oct. 3, 2022), 2 pgs.
"International Application Serial No. PCT/US2023/067550, International Search Report mailed Aug. 10, 2023", 2 pgs.
"International Application Serial No. PCT/US2023/067550, Written Opinion mailed Aug. 10, 2023", 4 pgs.
"International Application Serial No. PCT/US2023/067565, Written Opinion mailed Sep. 27, 2023", 4 pgs.
"International Application Serial No. PCT/US2023/067568, International Search Report mailed Sep. 29, 2023", 3 pgs.
"International Application Serial No. PCT/US2023/067568, Written Opinion mailed Sep. 29, 2023", 4 pgs.
Aldal, Inghild, et al., "Levels of androstenone and skatole and the occurrence of boar taint in fat from young boars", Livestock Production Science, 95(1), (2005), 121-129.
Andresen, Øystein, et al., "Boar taint related compounds: Androstenone/skatole/other substances", Acta Veterinaria Scandinavica, 48(Suppl 1):S6, (2006), 4 pgs.
Atanassova, N, et al., "Permanent Effects of Neonatal Estrogen Exposure in Rats on Reproductive Hormone Levels, Sertoli Cell Number, and the Efficiency of Spermatogenesis in Adulthood", Endocrinology, 140(11), (1999), 5364-5373.
At-Taras, Eeman E, et al., "Reducing Estrogen Synthesis in Developing Boars Increases Testis Size and Total Sperm Production", Journal of Andrology, 27(4), (2006), 552-559.
Berger, T, et al., "Increased testicular estradiol during the neonatal interval reduces Sertoli cell numbers", Anim Reprod Sci. 2018; 189:146-51., (2018), 146-151.
Bonneau, Michel, et al., "An international study on the importance of androstenone and skatole for boar taint: 1. Presentation of the programme and measurement of boar taing compounds with different analytical procedures", Meat Science, 54(3), (2000), 251-259.

Bonneau, Michel, et al., "Pros and Cons of Alternatives to Piglet Castration: Welfare, Boar Taint, and Other Meat Quality Traits", Animals, 9(11), 884, (2019), 12 pgs.
Candek-Potokar, Marjeta, et al., "Alternatives to surgical castration in pigs", Zivotnov'dni nauki, 52(5): 41-51, (2015), 13 pgs.
Cortes, ME, et al., "The Role of Kisspeptin in the Onset of Puberty and in the Ovulatory Mechanism: A Mini-review", J Pediatr Adolesc Gynecol., 28(5), (2015), 286-291.
D'anglemont De Tassigny, Xavier, et al., "Hypogonadotropic hypogonadism in mice lacking a functional Kiss1 gene", PNAS, 105(25), (2007), 10714-10719.
Daxenberger, A, et al., "Suppression of androstenone in entire male pigs by anabolic preparations", Livestock Production Science, 69(2), (2001), 139-144.
Garcia-Regueiro, JA, et al., "Evaluation of the contribution of skatole, indole, androstenone and androstenols to boar-taint in back fat of pigs by HPLC and capillary gas chromatography (CGC)", Meat Science, 25(4),, (1989), 307-316.
Gettys, T. W, et al., "Suppression of LH secretion by oestradiol, dihydrotestosterone and trenbolone acetate in the acutely castrated bull", J Endocrinol., 100(1), (1984), 107-112.
Grindflek, E, et al., "Revealing genetic relationships between compounds affecting boar taint and reproduction in pigs", Journal of Animal Science, 89(3), (2011), 680-92.
Hess, Rex A, et al., "Estrogens and development of the rete testis, efferent ductules, epididymis and vas deferencs", Differentiation 118, (2021), 41-71.
López-Bote, C, et al., "The reduction of boar taint in male pigs by neonatal testosterone administration", Meat Science, 22(3), (1988), 163-171.
López-Bote, C, et al., "Trenbolone Acetate Induced Changes in the Genital Tract of Male Pigs", Journal of Veterinary Medicine, Series B, 41(1-10), (1994), 42-48.
Minabe, Shiori, et al., "Long-Term Neonatal Estrogen Exposure Causes Irreversible Inhibition of LH Pulses by Suppressing Arcuate Kisspeptin Expression via Estrogen Receptors a and b in Female Rodents", Endocrinology, 158(9), (2017), 2918-2929.
Minabe, Shiori, "Neonatal Estrogen Causes Irreversible Male Infertility via Specific Suppressive Action on Hypothalamic Kiss1 Neurons", Endocrinology, 160(5), (2019), 1223-1233.
Novaira, Horacio J, et al., "Disrupted Kisspeptin Signaling in GnRH Neurons Leads to Hypogonadotrophic Hypogonadism", Mol Endocrinol, 28(2), (2014), 225-238.
Pantic, V., et al., "Testicular Structure and Serum Concentration of Gonadal Steroids in Male Pigs Neonatally Castrated or Treated with Estradiol and Progesterone", Bulletin de l'Academie Serbe des Sciences etdes Arts Classe des Sciences Naturelles et Mathematiques: Science Naturelles, vol. 25, pp. 57-72, (1984), 57-72.
Rasmussen, Martin, et al., "Regulation of Porcine Hepatic Cytochrome P450—Implication for Boar Taint", Comput Struct Biotechnol J., 11(19), (2014), 106-112.
Sheridan, PJ, et al., "The effect of anabolic agents on growth rate and reproductive organs of pigs", Livestock Production Science, 26(4), (1990), 263-275.
Stewart, Lawton, "Implanting Beef Cattle", UGA Cooperative Extension Bulletin 1302, (2013), 8 pgs.
Uenoyama, Yoshihisa, et al., "Central Mechanism Controlling Pubertal Onset in Mammals: A Triggering Role of Kisspeptin", Front Endocrinol (Lausanne), 10:312, (2019), 12 pgs.
Ventanas, J, et al., "Testicular development, androstenone levels and androstenone odour of untreated and trenbolone implanted boars", Journal of the Science of Food and Agriculture, 57(1), (1991), 127-133.
Williamson, DE, et al., "A selective immunization procedure against 5a-androstenone in boars", Animal Science, 35(3), (1982), 353-360.
Zamaratskaia, G, et al., "Plasma skatole and androstenone levels in entire male pigs and/relationship between boar taint compounds, sex steroids and thyroxine at various ages", Livestock Production Science, 87(2), (2007), 91-98.
"U.S. Appl. No. 18/324,786, Response filed Feb. 16, 2026 to Non Final Office Action mailed Nov. 17, 2025", 7 pgs.
"U.S. Appl. No. 18/324,798, Response filed Feb. 16, 2026 to Non Final Office Action mailed Nov. 17, 2025", 5 pgs.

(56)                 References Cited

OTHER PUBLICATIONS

"U.S. Appl. No. 17/937,743, Final Office Action mailed Mar. 19, 2025", 25 pgs.

"U.S. Appl. No. 18/324,798, Non Final Office Action mailed Nov. 17, 2025", 5 pgs.

"U.S. Appl. No. 19/334,213, Preliminary Amendment filed Dec. 8, 2025", 5 pgs.

"U.S. Appl. No. 18/324,786, Non Final Office Action mailed Nov. 17, 2025", 6 pgs.

"Brazilian Application Serial No. 1120240245314, Office Action mailed Mar. 9, 2025", w/ Machine English Translation, 2 pgs.

"Brazilian Application Serial No. 1120240245314, Response Filed May 16, 2025 to Office Action mailed Mar. 9, 2025", w/ Machine English Translation, 9 pgs.

"International Application Serial No. PCT/US2023/075842, International Preliminary Report on Patentability mailed Apr. 17, 2025", 13 pgs.

"U.S. Appl. No. 18/324,786, Notice of Allowance mailed Mar. 30, 2026", 8 pgs.

"U.S. Appl. No. 18/324,798, Notice of Allowance mailed Mar. 31, 2026", 8 pgs.

"U.S. Appl. No. 18/324,786, Corrected Notice of Allowability mailed Apr. 6, 2026", 2 pgs.

"U.S. Appl. No. 18/324,798, Corrected Notice of Allowability mailed Apr. 13, 2026", 2 pgs.

Reynolds, "The effect of trenbolone acetate on the bovine oestrous cycle", Animal Reproduction Science., vol. 4, No. 2 URL https www.sciencedirect.com science article abs pii 0378432081900373, Oct. 1, 1981, 10 pages.

Heitzman, R J, "The Effectiveness of Anabolic Agents in Increasing Rate of Growth in Farm Animals Report on Experiments in Cattle", Environmental Quality And Safety. Supplement, Thieme, Stuttgart, DE, No. 5, Jan. 1, 1976, 10 pgs.

Habert, "Effets des estrogenes sur le développement du testicule pendant la vie foetale et neonatale", Gynecologie Obstetrique and Fertilite, Elsevier Masson, FR, vol. 34, No. 10, With Machine English Translation, Oct. 1, 2006, 16 pgs.

Allrich, R. D, "Symposium Estrus, New Devices, and Monitoring Endocrine and Neural Control of Estrus In Dairy Cows 1", [Online]. Retrieved from the InternetURL http dx.doi.org https doi.org 10.3168 jds. S0022-03029477216-7, Sep. 1, 1994, 2738-2744.

"European Application Serial No. 23812819.3, Extended European Search Report mailed Feb. 25, 2026", 10 pgs.

"European Application Serial No. 23812820.1, Extended European Search Report mailed Feb. 2025, 26", 11 pgs.

NON-SURGICAL PREVENTION OF BOAR TAINT AND AGGRESSIVE BEHAVIOR

CROSS-REFERENCE TO RELATED APPLICATIONS

This application is a continuation of U.S. patent application Ser. No. 17/937,740, filed Oct. 3, 2022, which application claims the benefit of U.S. Provisional Application Ser. No. 63/365,389, filed May 26, 2022, which are incorporated by reference as if fully set forth herein.

BACKGROUND

Surgical castration is a medical procedure that is routinely performed on nearly all newborn male pigs. Castration or gonadectomy, which is performed without anesthesia or analgesia, is a crude, invasive animal husbandry (1) method that has been used for centuries to physically remove testes in the young piglets, primarily to prevent the development of 'boar taint' when the meat is cooked and to block the development of undesirable aggressive sexual behavior (2-4). Boar taint is the displeasing odor or taste that results from cooking pork from a certain percentage of boars (4, 5). This urine/fecal-like odor or taste is so offensive that removal of the source or cause is essential prior to sending mature male pigs (boars) to market. It was determined many years ago that removal of the testes prior to puberty greatly reduced boar taint and thus the procedure became routine, even before there was a clear understanding of all the molecules involved, other than reduction in testosterone (T) or androgens, which come from the testis. Subsequently, research has revealed that the primary sources of boar taint are not only androgens (4), in particular androstenone, but also skatole, a 3-methylindole conversion product of the amino acid tryptophan by gut bacteria (6-12).

Androstenone is an androgen hormone produced in the testes and is also considered a steroidal pheromone. Androstenone circulates as part of the endocrine system and can accumulate in the boar's saliva and body fat (12-14). Androstenone, which is uniquely found in high concentrations in boars, contributes to boar taint as it also builds up in adipose tissues, along with skatole (4, 15, 16). Skatole is produced in the gut and then absorbed into circulation (17), where it permeates all organs, but accumulates primarily in the fat in sexually mature boars. Skatole is removed metabolically in the liver, as it is oxidatively metabolized by cytochrome P450IIE1 (CYP2E1). However, androstenone inhibits this liver enzyme (17-19) and therefore, as boars reach sexual maturity, the increased production of T also increases androstenone, which results in the build-up of skatole in the fat because skatole metabolism is inhibited by androstenone (20, 21). In short, the boar taint odor occurs because both androstenone (22) and skatole build-up in the fat of boars before they go to market, where they are easily released when pork meat is cooked.

SUMMARY

One embodiment provides a method for inhibiting testicular development in the boar, which prevents the pubertal rise in blood and tissue androgens, and in particular androstenone, the major hormone responsible for boar taint, comprising injecting in said pig a combination of an androgen and an estrogen within the first week to 10 days after birth of said pig. In one embodiment, the injection is either subcutaneous or intramuscular.

One embodiment further comprises an implant wherein the implant comprises said androgen and estrogen, wherein the androgen and estrogen target both the hypothalamus-pituitary axis and testis development.

In one embodiment, the implant comprises a material or enclosure that maintains elevated circulating levels of compounds over nursery/nursing period (for example, no more than 12 weeks after birth, such as 4 to 12 weeks after birth, including 6-8 weeks). In one embodiment, the material or enclosure that provides sustained release consists with biodegradable polymers or biocompatible materials. In one embodiment, the material or enclosure that provides sustained release is a form of capsule, pellets, microspheres, gel, or solution. In one embodiment, the method of the excipient(s) and carrier(s) are suitable for the intended end use (i.e. food for human and/or animal) of tissue where injected.

In another embodiment, the injected androgen and estrogen are not present in the blood or tissues when the pigs are slaughtered.

In another embodiment, the androgen comprises testosterone, testosterone esters, testosterone metabolites such as 5α-dihydrotestosterone or their esters, trenbolone or trenbolone esters, or equivalents that have potent androgen activity. In one embodiment, the dose range of about 25-200 mg per pig.

In one embodiment, the estrogen comprises estradiol esters such as estradiol benzoate, estradiol valerate, estradiol cypionate, etc. In one embodiment, the dose range of about 1-40 mg per pig.

One embodiment provides that the injected amount of the androgen/estrogen combination is in a dose sufficient to inhibit the development of Kisspeptin neurons in the hypothalamus, LH production in the pituitary, Sertoli cell and Leydig cell proliferation in the testis and/or production of androstenone in the testis and accumulation of androstenone and skatole in the fat.

BRIEF DESCRIPTION OF THE DRAWINGS

The drawings illustrate generally, by way of example but not by way of limitation, various embodiments discussed in the present document. In the drawings, which are not necessarily drawn to scale, like numerals may describe similar components in different views. Like numerals having different letter suffixes may represent different instances of similar components.

DETAILED DESCRIPTION

Figure 1:
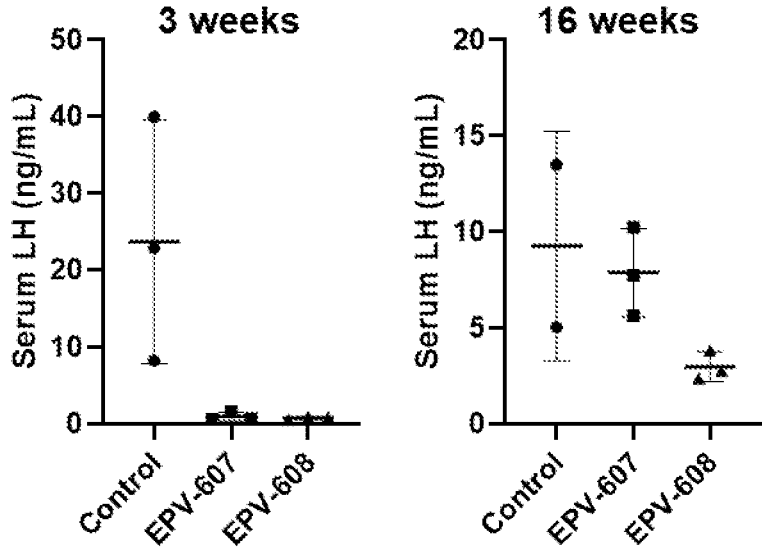
FIG. 1 illustrates exemplary pig serum LH concentration data from three subject groups (intact, EPV-607, EPV-608) at 3 or 16 weeks of age.

The following detailed description includes references to the accompanying drawings, which form a part of the detailed description. The drawings show, by way of illustration, specific embodiments in which the invention may be practiced. These embodiments, which may also be referred to herein as "examples," are described in enough detail to enable those skilled in the art to practice the invention. The example embodiments may be combined, other embodiments may be used, or structural, and logical changes may be made without departing from the scope of the present invention. While the disclosed subject matter will be described in conjunction with the enumerated claims, it will be understood that the exemplified subject matter is not intended to limit the claims to the disclosed subject matter. The following detailed description is, therefore, not to be taken in a limiting sense, and the scope of the present invention is defined by the appended claims and their equivalents.

The present invention pertains generally to preventing development of the boar testis and production and accumulation of the molecules that cause boar taint and induce aggression in males with age. Specifically, the invention relates to the inhibition of functional development of the pig testis by treatment with a combined use of androgen and estrogen in the newborn male piglet using extended drug delivery methods, for the purpose of inhibiting the production of testosterone (T) and androstenone, the accumulation of androstenone, a boar taint-inducing hormone, as well as skatole in the fat.

Definitions

In this document, the terms "a" or "an" are used to include one or more than one and the term; "or" is used to refer to a nonexclusive "or" unless otherwise indicated. In addition, the phraseology or terminology employed herein and not otherwise defined is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Reference in the specification to "one embodiment," "an embodiment," "an example embodiment," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt. % to about 5 wt. %, but also the individual concentrations (e.g., 1%, 2%, 3%, and 4%) and the sub-ranges (e.g., 0.1% to 0.5%, 1.1% to 2.2%, and 3.3% to 4.4%) within the indicated range.

The term "about" as used herein can allow for a degree of variability in a value or range—for example, within 10%, within 5%, within 1%, within 0.5%, within 0.1%, within 0.05%, within 0.01%, within 0.005%, or within 0.001% of a stated value or of a stated limit of a range—and includes the exact stated value or range.

As used herein, an "effective amount" means an amount sufficient to inhibit the production of boar taint causing molecules. An effective amount can be administered in one or more administration. In some embodiments, an effective amount of androgen and estrogen can be achieved in conjunction with another drug, compound, or pharmaceutical composition. In other embodiments, an effective amount of androgen and estrogen may be achieved in isolation from the use of another drug, compound, or pharmaceutical composition.

The term "EPV-607" as used herein refers to a product that comprises a combination of 25-200 mg testosterone propionate and 1-40 mg estradiol benzoate with a slow releasing carrier/matrix.

The term "EPV-608" as used herein refers to a product that comprises a combination of 25-200 mg trenbolone acetate and 1-40 mg estradiol benzoate embedded in a slow releasing carrier/matrix.

The terms "carrier," "pharmaceutically acceptable carrier," or "physiologically acceptable carrier" as used herein refer to one or more formulation materials suitable for accomplishing or enhancing the delivery of androgen and estrogen as composition (i.e., pharmaceutical composition).

Compositions and Methods

It is important to not only prevent the accumulation of androstenone and skatole in the fat but also to prevent androstenone from inhibiting the metabolism of skatole in the liver. Therefore, the androgen androstenone is a major target molecule for the development of any alternative to surgical castration. If a substitute medical procedure, e.g., implanting a hormonal mixture for temporal release, causes a decrease in plasma androstenone concentrations, it will allow skatole to be metabolized by the liver and excreted from the body, which will reduce the presence of boar taint in the meat.

In boars, androstenone concentrations are positively correlated with the levels of T and skatole in blood plasma from approximately 14 to 24 weeks of age, and skatole and androstenone levels are highly correlated in fat at slaughtering ages of 20-24 weeks (12). Therefore, inhibiting testicular development and consequently Leydig cell function would be ideal for preventing the accumulation of the molecules responsible for producing boar taint in the fat, as well as reducing the undesirable aggressive behavior seen as boars mature (23-26).

To inhibit the development of boar taint in mature pigs, it is necessary to use some type of medical intervention that will reduce the synthesis and accumulation of androstenone. This singular inhibition will permit the liver to carry out its natural activity of metabolizing skatole and reduce the accumulation of skatole and androstenone in the fat. It is for this reason that surgical castration became a routine procedure on swine farms, as it was the only quick, inexpensive and effective way to control boar taint in the meat from male pigs. It is common knowledge that pork from non-castrated males is unacceptable in most of the pork industry (27-29). Removal of the testes eliminates Leydig cells, which are responsible for the synthesis of androgens, T, and its metabolite androstenone (4, 12, 30-32). This veterinary medical procedure of castrating male pigs is routine husbandry performed during the first week after birth because it is generally assumed that the piglets experience less pain than older pigs and the smaller animals are without a doubt easier to handle (33, 34). However, castration, which is performed on the farm without anesthesia or analgesic, does induce pain in the piglets (35, 36) and affects animal behavior for several weeks (37).

There has been considerable effort to find a replacement for the surgical castration procedure in pigs, with animal welfare being one of the major concerns (3). However, finding an alternative that could replace the procedure must take into consideration several potential organ targets that could disrupt the production of androgens, including the hypothalamus, pituitary and testis.

Inhibition Target 1: Hypothalamus and Pituitary. The invention is focused on a pharmaceutical intervention that inhibits the development of the testis. Reproduction in mammals is regulated by hormones that are released from the Hypothalamus region of the brain, the nearby Pituitary, and the distal Gonads that must be exposed to pituitary hormones via blood circulation. This physiological system is called the HPG axis. A hormone produced in one area of the HPG axis either stimulates or inhibits the secretion of a hormone in the other organ via a regulatory loop, called positive and negative feedback loops, respectively. Hypothalamic neurons produce two key reproductive hormones, Kisspeptin (KISS1) and GnRH (Gonadotropin-Releasing Hormone) (38-41). In a unidirectional regulation, KISS1 is secreted, binds to the KISS1 receptor (GPR54) in the cell membrane of the GnRH neurons, and triggers the release of GnRH. Importantly, ablation of either Kiss1 or Gpr54 genes results in hypogonadism and sterility (42, 43). GnRH travels down to the pituitary via a local portal vein and triggers the secretion of LH (luteinizing hormone) and FSH (Follicle-Stimulating Hormone), which collectively stimulate the gonads to grow and produce sex steroids, primarily T and androstenone in male pigs, and to promote the production of sperm.

The target in the hypothalamus is neuropeptide KISS1 produced by Kisspeptin neurons, which initiates puberty by directly stimulating the release of GnRH (44-46). Thus, KISS1 is integral in facilitating the correct timing of puberty and normal gonadal development. Knockout of the Kiss1 gene, responsible for encoding KISS1, or its receptor, GPR54 in the GnRH neurons, was shown to result in sterility in both male and female mice (43, 47-51). The loss of KISS1 expression in the male results in significantly lower plasma levels of LH and T, which results in male infertility (52, 53).

Temporary treatment with exogenous estrogen targets the hypothalamus Kisspeptin neurons, permanently reducing KISS1 and subsequently GnRH and LH secretion, eventually lowering testicular T production and serum T levels long-term (54). Neonatal treatment with a synthetic androgen, such as Trenbolone, Trenbolone acetate (TBA) or 5α-dihydrotestosterone (DHT), targets the pituitary and thus also helps to inhibit LH release by making the pituitary insensitive to GnRH stimulation (55, 56). Neonatal treatment with an estrogen, such as estradiol benzoate, targets the hypothalamus in mammals (54, 57, 58), but in pigs estrogen is also capable of targeting Sertoli cells in the testes (59-63). Therefore, neonatal treatment includes an androgen, as well as an estrogen, as the active pharmaceutical ingredients (API) for this innovation, because together they will inhibit hypothalamus Kisspeptin neuron development, the pituitary gonadotrophic cell's release of LH and testicular somatic cell development. This will provide a long-term inhibition of the first wave of Leydig cell proliferation and maturation (64). The same estrogen plus an androgen will effectively inhibit KISS1 expression and consequently LH secretion in females as well, eventually causing them not to exhibit estrous cycle.

Inhibition Target 2: Testis. The core organs of the male reproductive system are testes, which undergo dramatic developmental and structural changes from birth to puberty. Testicular development produces four major cell types: 1) germ cells, surrounded and nurtured by 2) Sertoli cells, which together with germ cells compose the seminiferous tubules; 3) thin, peritubular myoid cells that surround a basement membrane of the seminiferous tubule; and 4) Leydig cells, located between the tubules and blood vessels (65-67).

In testes, Leydig cells are the major androgen producing cells. They serve as the source of T and androstenone synthesis (7-9, 11, 12, 16, 68-70). These androgen hormones are found in nearly equal concentrations in boar blood (71) and show distinctive increases as the male pigs age from birth to puberty, peaking as they reach maturity, coinciding with when pigs are typically ready for shipping to market (11). However, normal Sertoli cell development is also required for proper proliferation and differentiation of Leydig cells (72-76).

Before birth, testicular development is independent of the HPG axis, but starting at birth the HPG hormones are clearly established as major regulatory factors in testicular growth (53). The postnatal surge in serum T is dependent on the KISS1 stimulation of GnRH secretion and the release of LH, which stimulates fetal Leydig cells still present in the newborn testis to produce high levels of T for masculinization of the young male (77). In the pig, the secretion of LH and FSH then declines over the first 5 weeks (78), but rises again peaking at about 10-14 weeks to coincide with the formation of adult Leydig cells from progenitor cells that divide during the prepubertal period (64, 79-82). Thus, the most effective method for reducing testicular production of androgen hormones requires inhibition of the first wave of proliferation, and inhibition and/or delay of the second wave by extending the treatment from neonatal age to at least through the nursery period. In addition to Leydig cells, during this neonatal period, Sertoli cells also experience a major stimulation of activity. Sertoli cells go through two waves of proliferation, the first from before birth increasing until just after birth and then declining out to 4-5 weeks, and the second wave just before puberty. In rodents, FSH is the primary stimulus of Sertoli cell proliferation during the neonatal period, which is essential for normal testis size. However, in the pig estradiol (E2) and other growth factors have more important roles in the regulation of testis development, uniquely focused on the Sertoli cells.

Male pig testes produce high concentrations of E2 (12, 71, 83-85), primarily synthesized by the Leydig cells, which have high aromatase activity from birth to about 4 weeks (86). E2 concentrations are especially elevated during this neonatal period (87). Research into estrogen's role in testis development in the pig demonstrated an unusual function in helping to regulate Sertoli cell proliferation, which helps to carefully maintain a balance in the total number of Sertoli cells. Treatment of the young male pigs with Letrozole, an aromatase inhibitor, or a pure anti-estrogen ICI 182,780, which reduces E2 synthesis or blocks the estrogen receptor, results in a highly significant increase in the duration of Sertoli cell proliferation and testis size, allowing Sertoli cells to proliferate for a longer period of time (59-63). However, interference with the pig testis production of estrogen required extended treatment for at least 4 weeks (62). Furthermore, treatment of neonatal pigs with exogenous E2 produces the opposite effect resulting in a significant decrease in the number of Sertoli cells (60). This was a direct effect on the cells, as Sertoli cells express the estrogen receptor alpha (ESR1) during this period of development (88). As Sertoli cells differentiate into mature cells, they become resistant to FSH stimulation of proliferation (89) and depend on the androgen T for the maintenance of spermatogenesis and germ cell development (90). Leydig cells are responsible for the production of androgens, in particular T and androstenone, and in the pig increased levels of E2 (converted from T by aromatase) (91). Thus, neonatal treatment with exogenous estrogen in the male piglet has a direct inhibitory effect on Sertoli cell proliferation, as well as inhibiting the development of the hypothalamus/pituitary axis.

If the treatment is performed as a replacement of the neonatal castration procedure, the combination of an androgen and estrogen is essential for sustained inhibition of production of the molecules that cause boar taint. The pig shows specific, and significant differences in hormonal regulation of testicular development compared to other mammals, although the overall hormonal regulation of the male reproductive system is common across mammalian species. Development of the testis in most mammalian species follows a well-understood endocrine-driven pathway, which is especially well-studied in rodent species, as they are the common basic research model. In rodents, it is well-established that FSH is a major driver for Sertoli cell proliferation and LH is the key factor in Leydig cell development (92, 93). Sertoli cells serve as nurturing cells for germ cells (94) and each Sertoli cell supports a finite number of germ cells (95). Thus, it is the total number of Sertoli cells that determines the ultimate size of the testis (72). Furthermore, the number of Sertoli cells indirectly regulates the number of Leydig cells (72, 74, 96). Thus, regulation of Sertoli cell numbers in the developing pig testis is just as important as inhibiting Leydig cell function. However, regulation of testis development in the pig shows some specific differences from rodents and other mammalian species, such as E2 having a direct inhibition of Sertoli cell proliferation, as demonstrated by aromatase inhibitor treatment causing an increase in Sertoli cell numbers (60).

Even signaling through the androgen receptor (AR) in the pig from birth to 11 weeks is different, as treatment with Flutamide (AR inhibitor) also increased the number of Sertoli cells (97). However, although the Flutamide effect appears to be directly in the testis (as an FSH increase occurred after the increase in Sertoli cell proliferation), it must have been indirect because Sertoli cells at this age have a low expression of AR (88). This suggests that an androgen could also have direct effects on the testis, but indirect on the Sertoli cells. For example, androgen directly inhibits the differentiation of progenitor Leydig cells (98) and induces germ cell apoptosis (99). In the immature pig, stimulating the AR also has the ability to inhibit Sertoli cells, as demonstrated by treatment with Flutamide (97).

Inhibition and delay of pig testis development from birth to slaughter time (approximately 26 weeks of age), as in the case of replacing neonatal castration, requires targeting the entire hypothalamus/pituitary/testis axis, otherwise there will be inconsistent results and potential for regrowth prior to the slaughter age. To accomplish this goal, male piglets have to be treated with a combination of an androgen and estrogen via a carrier that releases those hormones for a certain period. The residual amount of the hormones and the carrier in the treated pigs must be below a level that is imposed or regulated by governing authorities such as FDA and/or USDA in the United States. TBA is a synthetic androgen that has both direct effects on the testis and a more rapid inhibitory effect on the release of LH in the pituitary. Estradiol benzoate (EB) is a long-acting estrogen that will deliver long-term inhibition of the hypothalamus for reducing LH production, but also provide direct inhibition of Sertoli cell proliferation, thereby decreasing Sertoli cell numbers and indirectly decreasing the number of Leydig cells and inhibiting and/or delaying their differentiation at the onset of puberty. Thus, the combined treatment is capable of inhibiting all three components of the HPG axis and must be delivered neonatally with extended, but temporary elevation of circulating levels of the compounds that inhibit the two waves of Sertoli and Leydig cell proliferation and the onset of testicular maturation. This treatment inhibits testicular development, and importantly the active pharmaceutical ingredients (APIs) disappear from the body before slaughter.

Understanding these differences in pig testis development was relevant to designing an innovative treatment to inhibit testis development and synthesis of T and androstenone. In neonatal rodents, the proliferation of Sertoli cells is correlated with a neonatal rise in FSH and the treatment of newborn rodents with FSH stimulated Sertoli cell proliferation, nearly doubling testis weight (100, 101). Because Sertoli cells serve as nurturing cells for all germ cells, their total number determines the ultimate size of the testis (72); thus, the increase in their proliferation is the cause of increased testis size. Furthermore, the number of Sertoli cells indirectly regulates the number of Leydig cells (72, 74, 96). Because Leydig cells are responsible for the synthesis of T and androstenone in the boar testis, decreasing their numbers is the first step in this innovative procedure. In the pig, although Sertoli cell numbers also regulate Leydig cells numbers and steroidogenic activity (102), in contrast to rodent species, pig Sertoli cell proliferation precedes the rise in FSH, with FSH progressively declining from birth (103, 104) and FSH treatment of the neonatal pig showed little to no effect on Sertoli cell proliferation and the testis size (90, 104-107). Thus, the pig does not depend on an increasing concentration of FSH for stimulating Sertoli cell proliferation. Instead of FSH, decreasing E2 levels using an anti-aromatase chemical or blocking ESR1 (the estrogen receptor) during the first wave of Sertoli cell proliferation increased their numbers and treatment with exogenous E2 caused a decrease in the number (59-63). Therefore, treatment neonatally with EB (or equivalent estrogen) is required as one of the APIs, because the proliferation of the pig Sertoli cell is not dependent on rising FSH in the postnatal and prepuberal periods but is inhibited by E2.

Estrogen concentrations are naturally high in male pig blood and pig reproductive organs (12, 71, 83-85), which results in minimal hypothalamus/pituitary feedback regulation in the pig (59). Thus, the pig depends on an alternative regulation of Sertoli cell proliferation. Pig Sertoli cells express ESR1 in the prepubertal testis and are directly responsive to E2 during development (60, 88), while Sertoli cells of the rodent testis lack ESR1 (108). Thus, the pig testis shows direct sensitivity to neonatal E2 (60), while the rodent testis shows only indirect effects (109). Although the pig hypothalamus shows little negative feedback inhibition of FSH, Kisspeptin neurons are present and neonatal treatment with E2 showed a decrease in KISS1 expressing cells in the caudal region of the ARC and a decrease in LH secretion (38, 39). Thus, inhibition of the development of Kisspeptin neurons will provide long-term inhibition of GnRH stimulation of the pituitary synthesis and release of LH (54), providing a method for inhibiting the second wave of Leydig cell proliferation.

Inhibition of pig testis development post-birth requires a period of treatment that would cover both the Sertoli cell and Leydig cell proliferation periods but is short enough to permit the treatment compounds to disappear prior to the animal reaching sexual maturity. The pig Sertoli cell population is established over an extended period of time between birth and the onset of puberty by experiencing two waves of proliferation, apparently only requiring high levels of FSH at birth, which then declines during the first wave period. Then FSH starts rising again at 10 weeks (110), correlating with the onset of the second wave of Sertoli cell proliferation and subsequent maturation and establishment of the blood-testis-barrier junctions to support spermatogenesis (111, 112). The Sertoli cell marker for immaturity, Anti-Müllerian Hormone (AMH), also declines as the males reach 12 weeks of age (112, 113). Leydig cells on the other hand are dependent on LH stimulation, local growth factors (31, 78, 114), and Sertoli cell influence (the factor thus far unidentified). Leydig cells show proliferation and differentiation over the same extended period prior to puberty, similarly in two-wave formations, with their numbers having a high correlation with testis weight (115). The first wave of Leydig cell proliferation and function produces an increase in T from birth to about 1 week and then there is a dramatic decrease. The second wave begins at about 12 weeks with Leydig cell proliferation and differentiation into adult Leydig cells that produce the dramatic rise in T just before puberty (64, 83, 86, 116, 117). Leydig cells are stimulated by a rise in circulating LH, which is consistent with the two waves of increased T (77). In pigs, LH rises dramatically at birth and stays elevated for several weeks before declining (78). Such neonatal rise of LH can be inhibited by the co-treatment of an androgen+estrogen. By treating with an androgen+estrogen in a slow-release profile, it is possible to limit not only the LH rise, but also both Sertoli and Leydig cell proliferation waves in the pig, if given soon after birth.

Although such treatment in older males (up to 19 weeks of age) decreased testis size, inhibited Leydig cell function and decreased serum T levels, it was unacceptable, because timing of the treatment was too close to the pig's slaughter age, which risks having a significant residual amount of the hormones in the meat (118).

Others have used androgen and estrogen combinations in attempts to inhibit testis function. However, in these three studies the treatment was given to older boars, and to neonatal pigs, the age at which castration is performed (118-121). After treatment, at 27 weeks of age, a decrease in testis weight was reported and there was also a decrease in serum T and decrease in fat content of androstenone. The Ventanas study also reported that the backfat of treated animals gave off no significant androstenone odor (121). Another study implanted the older boars at 19 weeks of age with either testosterone propionate (TP) plus EB or TBA plus EB. TBA but not TP with EB treatment resulted in significant decreases in serum T and androstenone at slaughter; however, neither treatment resulted in significant change in testis weight at slaughter. While the studies with TBA and TBA+EB treatment gave desirable results, treatment in the older boars cannot be used for the reduction in boar taint, because there is a risk that a significant amount of residual compounds can yet to be present in the meat at slaughter (118). Furthermore, restraining pigs at the ages of 14 weeks or later for the injection of the compounds is physically challenging because the intact boars at those ages are large in size, dangerously heavy and aggressive. Thus, there are two major reasons why treating pigs at a neonatal age will be beneficial: (1) the API will no longer be present in the animal at slaughter and (2) the piglets will be less aggressive and easier to handle and not place workers in as great a risk of injury. To be successful with neonatal treatment, which is desirable if the routine practice of castration in newborn piglets is to be replaced, the implant must inhibit the growth of testis and the first wave of Leydig cell proliferation that begins soon after birth (64, 83, 86, 117) and the second wave that begins around 12 weeks (64, 83, 86, 116, 117). This concept is important because the first wave of Leydig cells consists of immature/progenitor cells (122) that express the 5α-reductase enzyme required for androstenone synthesis (123-125). Therefore, to prevent early and long-term androstenone synthesis, the first wave of Leydig cell development, as well as the second wave needs to be inhibited by using neonatal treatment with both an androgen and an estrogen.

In two other published studies, treatments were given on day 1 of birth. However, these two papers must be viewed with caution because the exact same data was published in both papers, which would be an unethical duplication of data. Table 2 of the 1988 paper (15) and Table 1 in the 1992 paper (126) contain identical data. In both publications, they injected subcutaneously the synthetic androgen, TP, in male piglets on day 1 of birth and the reproductive system was evaluated at 25 weeks of age (15, 126). It was noted that much of the claims of these two papers were not supported by the data presented: the standard errors for testis weights and T concentrations were very wide (pointed out also by the authors) and although the authors claimed that there was a permanent reduction in LH, no supporting data or immunohistochemical photos were provided. One standard deviation for testis weight in the treated males would put some treated testes at 192 g, while the mean weight of the control testes was only 188 g. The paper stated that there was a treatment related decrease in germ cells, but no histological evidence was shown. The studies also failed to determine androstenone concentrations, the primary androgen responsible for the development of boar taint and provided no quantitative or statistical analysis for boar taint detection.

In previous studies, TP treatment of newborns piglets would have been a problem because its androgenic activity would be limited due to the unique biological characteristics of neonatal male pigs. In the neonatal pig hypothalamus, males have higher aromatase activity than female, thus the tissue quickly converts testosterone into estrogen (127, 128). Furthermore, fetal testis express aromatase protein, and the expression level sharply increased from 10 weeks of gestation until birth (129). These indicate that aromatizable androgen may lose androgenic potency due to the active conversion into estrogen by aromatase activity in the neonatal piglets. Indeed, in the example of this invention, TP (aromatizable androgen) was not as potent as TBA (non-aromatizable androgen) in reducing circulating levels of LH levels at 16 weeks. This indicates that non-aromatizable androgen will be more potent than an aromatizable androgen for inhibition of male gonad development. Therefore, the combination of a non-aromatizable androgen and estrogen, rather than the combination of aromatizable androgen and estrogen, maximizes the efficacy of the neonatal treatment for the purpose of inhibiting testis development until slaughtering age.

Currently, there are no non-surgical castration techniques available that have a high degree of certainty for both disrupting Kisspeptin neuron development or KISS1 expression, decreasing LH production, as well as directly inhibiting the development of testicular cellular components. The proposed invention provides a simple, easy-to-implement, pharmaceutical intervention that can replace currently used procedures of surgical castration in newborn pigs and immunocastration of older boars. A single injection of the two compounds in a sustained-release carrier will inhibit long-term/irreversibly the activation of the HPG axis, inhibit Sertoli cell proliferation, and disrupt Leydig cell development and steroidogenic function of the testis. This treatment strategy will prevent the accumulation in fat of the molecules that cause boar taint and block the development of aggression in maturing male pigs.

The present invention pertains generally to preventing development of the boar testis and inhibit production and accumulation of the molecules that cause boar taint and aggression as the males increase in age. Specifically, the invention relates to the inhibition of functional development of the pig testis by treatment with a combined use of an androgen and estrogen in the newborn male piglet using extended drug delivery methods, for the purpose of inhibiting the production of T and androstenone, the accumulation of androstenone, a boar taint-inducing hormone, as well as skatole in the fat. The same treatment will prevent females from exhibiting estrous cycling.

The drug pellet, microsphere, gel, or solution (hereafter, drug complex) comprises biocompatible-/biodegradable polymers or solvents.

The drug complex comprises a hormone-based compound configured to inhibit the postnatal release of LH from the pituitary, development of hypothalamic Kisspeptin neurons and cellular components of the testis.

The drug complex allows for the sustained but temporary release of the steroids into a body of an animal once the drug-carrier has been injected or implanted therein.

Embodiments of the invention comprise insertion methods configured to allow injection of a drug complex through larger epidermal layers or muscle In some embodiments of the invention, the drug complex may comprise EB and TBA. In other embodiments, the drug complex may comprise other forms of androgens and other estrogen esters. In some embodiments, the drug complex is injected into the subject within the first week to 10 days after birth when piglets are receiving vaccines, tail docking, and other early animal husbandry care.

Embodiments of the invention may include subjects such as swine, bovine, lamb, or goat; while other embodiments of the invention may further include subjects physiologically similar to said subjects.

The invention involves the inhibition of testicular development and thereby the prevention of a rise in blood and tissue androgens such as T and androstenone by treating newborn male piglets with a combination of an androgen and a long-acting estrogen in a delivery method that allows for sustained, but temporary elevation of the compounds over a nursery period (4-12 weeks). The combined steroids, androgen and estrogen, permit the targeting of both the hypothalamus/pituitary region, as well as the testes directly (through both the Sertoli and Leydig cells).

Concentration/Amount of Estrogen and/or Androgen

Boar taint and aggression inhibiting compositions comprise of an androgen and estrogen. An effective amount of androgen and estrogen to induce the required inhibition of testis development and androgen production can depend, for example, the route of administration, the age of the animal, and its size (body weight). Accordingly, the skilled artisan may titer the dosage and modify the route of administration of an androgen and estrogen to obtain the optimal effect for a particular animal.

A typical dosage of androgen (TBA, as an example) may range from about 25 mg/kg to up to about 200 mg/kg or more. In other embodiments, the dosage of androgen may range from 25 mg/kg up to about 200 mg/kg; or 100 mg/kg up to about 200 mg/kg; or 150 mg/kg up to about 200 mg/kg. In pigs the dose can range from about 25 mg to about 200 mg per animal, including about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, or about 200 mg per animal.

A typical dosage of estrogen (EB as an example) may range from about 1 mg/kg to up to about 40 mg/kg or more. In other embodiments, the dosage of EB may range from 1 mg/kg up to about 40 mg/kg; or 10 mg/kg up to about 40 mg/kg; or 15 mg/kg up to about 40 mg/kg; or 30 mg/kg up to about 40 mg/kg. In pigs the dose can range from about 1 mg to about 40 mg per animal, including about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, or about 40 mg per animal.

Timing of Administration

Compositions comprising androgen and estrogen to reduce taint and/or aggression are administered prior to puberty (prior to reaching sexual maturity/capable of reproduction). The compositions can be administered neonatally. Administration of an androgen and estrogen effectively inhibits/blocks maturation of sex organs/gonads in males.

Route of Administration

The route of administration of the composition provided herein is in accordance with known methods, e.g., injection (intraperitoneal, intramuscular, subcutaneous) and nasal (inhalation). In one embodiment, an androgen and estrogen are administered for inhibition of boar taint and/or aggression of an animal in a single, one-time dose. In other embodiments, multiple administrations of an androgen and estrogen can be carried out to inhibit testis development, boar taint and/or aggression.

Compositions

In one embodiment, an androgen and estrogen compositions for injectable administration can be in the form of oleaginous suspensions, including oil, such as vegetable oil (e.g., corn oil), cottonseed oil, peanut oil, and/or sesame oil. Other carriers or fillers can be used instead of, or in addition to, oil. Carriers/fillers can include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol. These suspensions can be formulated according to methods available to the art for dispersing and suspending ingredients.

In another embodiment, the composition described above can be encapsulated for administration. In one embodiment, a capsule can be formed from silicone tubing with plugs at each end to contain a mixture of, for example, androgen, estrogen, and oil. The capsules can be placed, such as by injection (further described below), in the body of the subject. The androgen and estrogen compositions described herein can be formulated for immediate release or in a time release formulation (e.g., slow release). For example, an androgen and estrogen can be prepared with carriers that protect the androgen and estrogen against rapid release, such as a controlled release formulation.

Many methods for the preparation of controlled/slow-release formulations are known to those skilled in the art. For example, techniques for formulating a variety of sustained- or controlled-delivery means, such as liposome carriers, polymers (e.g., ethylene vinyl acetate, polyanhydrides, silicone, polyglycolic acid, collagen, polyorthoesters, poly-lactic acid and polylactic, polyglycolic copolymers (PLG)), microparticles, nanoparticles (such as nanospheres, including biodegradable nanospheres or porous beads, and depot injections) are also known to those skilled in the art. For example, see PCT/US93/00829, which describes controlled release of porous polymeric microparticles for the delivery of pharmaceutical compositions. Additional examples of sustained-release preparations include semipermeable polymer matrices in the form of shaped articles, e.g., films or microcapsules. Sustained release matrices may include polyesters, hydrogels, polylactides (U.S. Pat. No. 3,773,919, EP 58,481), copolymers of L-glutamic acid and gamma ethyl-L-glutamate (130), poly (2-hydroxyethyl-methacrylate) (131, 132), ethylene vinyl acetate or poly-D(−)-3-hydroxy-butyric acid (EP 133,988). Sustained-release compositions also include liposomes, which can be prepared by any of several methods known in the art. See e.g., Epstein et al., (133), 1985; EP 36,676; EP 88,046; EP 143,949.

One embodiment provides kits for producing a single-dose administration unit. The kits may contain single and multi-chambered pre-filled syringes containing an androgen and estrogen and instructions for use (inhibiting testis development and reducing boar taint).

EXAMPLES

Example 1—Effects of Injecting Androgen (Aromatizable and Non-Aromatizable)+Estrogen in Neonatal Piglets Via Carrier on the Serum LH Level EPV-607 is an injectable implant, composed of excipient for slow/delayed release and two APIs: 100 mg TP (CAS #57-85-2) and 10 mg EB (CAS #50-50-0). EPV-608 is an injectable implant, composed of excipient for slow/delayed release as the excipient and two APIs: 100 mg TBA (CAS #10161-34-9) and 14 mg EB (CAS #50-50-0).

Treatment of animals. Neonatal male piglets (Large White X Landrace) were treated with EPV-607 or EPV-608 on 1 day after birth by subcutaneous injection on the backside of the neck (n=3). The injection site of the pellet was then sealed using surgical sealant. There were two control groups; 2 piglets castrated 1 day after birth and 4 untreated piglets that remained as intact controls. All piglets were raised in the same pen until they reached slaughter age. Blood was collected on week 3 or 16 to measure the concentrations of LH.

LH measurement. Serum LH levels were measured by Pig LH ELISA (LS-F34361, LSBio Inc., WA). Data are presented using descriptive analysis as well as mean±SD.

Results

Control intact animals had 23.7±15.86 ng/ml serum LH concentration at 3 weeks of age (FIG. 1). In contrast, animals treated with either EPV-607 or EPV-608 had 96% (0.96±0.55 ng/mL) and 97% (0.75±0.17 ng/mL) lower serum LH concentrations, respectively, than control intact animals. At 16 weeks of age, the LH levels of animals treated with EPV-607 (7.87±2.30 ng/ml) was similar to those of intact pigs (9.27±5.98 ng/mL), whereas animals treated with EPV-608 showed 68% lower LH levels (2.98±0.77 ng/mL) than those of intact pigs.

The function of the pituitary gonadotropic cells, especially synthesis and secretion of LH, is crucial for testis development and steroidogenesis in pigs. Therefore, in order to inhibit T and androstenone synthesis in the testis by reducing circulating LH levels, either EPV-607 or EPV-608 are applicable. However, EPV-608 which contains non-aromatizable androgen showed more prolonged effects in reducing circulating LH levels than EPV-607 which contains aromatizable androgen.

Example 2—Effects of EPV-608 on the Production of Boar Taint Molecules. TBA+EB Implant—EPV-608

For this experiment, TBA+EB was given in an injectable solid pellet (EPV-608) composed of excipient for slow/delayed release, 100 mg TBA (CAS #10161-34-9) and 14 mg EB (CAS #50-50-0).

Treatment of animals. Neonatal male piglets (Large White X Landrace) were treated with EPV-608 on 1 day after birth by subcutaneous injection on the backside of the neck (n=3). The injection site of the pellet was then sealed using surgical sealant. There were two control groups; 2 piglets castrated 1 day after birth and 4 untreated piglets that remained as intact controls. All piglets were raised in the same pen until they reached slaughter age. Blood, saliva and ear punches were collected starting on week 24 to measure the concentrations of T and androstenone.

Slaughter and measurement. Boars were slaughtered at 26 weeks of age. Blood and organs were harvested and weighed, including testes. Serum was obtained from the blood samples following centrifugation. Fat tissues were collected from underneath the abdominal skin. Serum T levels were measured by ELISA (EIA1559, DRG International, NJ). Ear biopsy and saliva androstenone levels were measured by liquid chromatography-mass spectrometry (LC-MS/MS) and reported as ng/g. Given the well documented natural variation that occurs in untreated boars, data are presented using descriptive analysis as well as mean±SD. Where appropriate, statistical significance was determined by One-way ANOVA.

Results

A single injection of EPV-608 into neonatal pigs resulted in smaller testes and reduced levels of the steroid hormones T and androstenone, which are naturally produced in higher concentrations by the testis, as boars reach sexual maturity.

Figure 2:
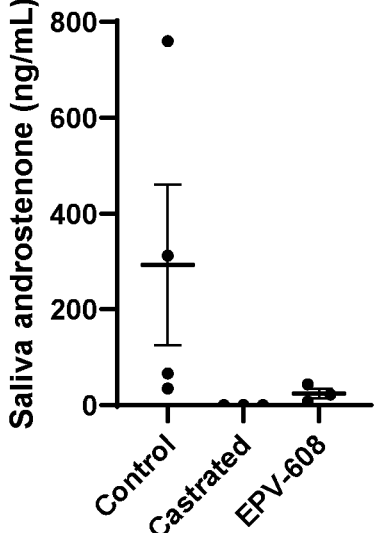
FIG. 2 illustrates exemplary male pig saliva's androstenone concentration data from three subject groups (intact, castrated, EPV-608) at 24 weeks of age.

Androstenone is the major hormone that drives the development of boar taint (4). Androstenone is produced in the testis, released into the blood, and in the liver inhibits the metabolism of skatole, and then the hormone accumulates in fat along with skatole, but it is also found in high concentration in salivary glands because it also serves as a steroidal pheromone in boar's saliva (8, 9, 14, 17, 18, 134, 135). In the Control intact animals at 24 weeks of age, saliva from 2 of 4 males (50%) had androstenone levels that were greater than 200 ng/ml (293.4±1267.4 ng/mL) (FIG. 2), indicating that these animals were developing boar taint characteristics and the meat would ultimately be unsatisfactory to consumers. The observed variation of androstenone concentrations in intact animals was expected and is consistent with the literature. In the EPV-608 treated boars, the concentration in saliva was significantly less than 200 ng/ml in all the males. The mean concentration of salivary androstenone (24.47±10.43 ng/ml) in EPV-608 treated animals was 91% lower than in the intact controls. In the surgical castrated piglets, in which the source of production was removed, saliva androstenone was not detected.

Figure 3:
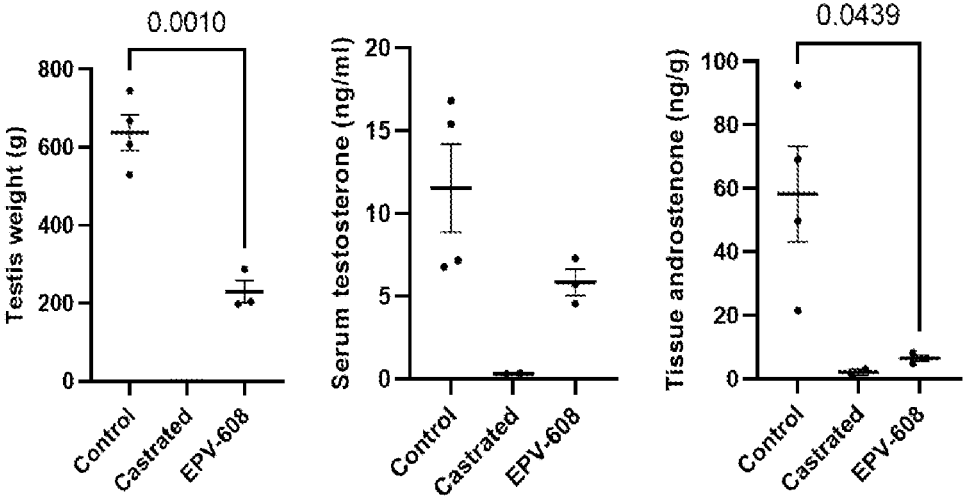
FIG. 3 illustrates exemplary pig testis weight, serum testosterone concentration, and tissue androstenone data from three subject groups (intact, castrated, EPV-608) at 26 weeks of age.

To test the effects of EPV-608 at 26 weeks of age (the industry standard age for slaughter), the animals were sacrificed, and samples collected for analysis. The testes were weighted; T concentrations were determined in blood serum; and androstenone concentrations were measured in back fat tissue. Testes weights in the EPV-608-treated boars were 63.9% smaller than in the control intact males, with a mean EPV-608 testis weight of 230.0±29.05 g, compared to 637.5±45.51 g for testes of control boars (FIG. 3).

Consistent with the salivary androstenone results, control boars at 26 weeks of age showed considerable variation in the concentrations of serum T, with the 2 controls showing high levels of androstenone also showing higher levels of T. In contrast, all of the EPV-608 treated boars had nearly 50% lower levels of T (FIG. 3). In controls, the mean serum T concentration was 11.53±2.6 ng/mL, while in EPV-608 treated pigs the T mean was 5.85±0.80 ng/mL. However, due to the high variation seen in the controls and the small sample sizes, the results were not statistically significant. The castrated group, as expected had the lowest T levels (0.33±0.02 ng/mL).

Tissue androstenone levels at 26 weeks displayed a pattern similar to that found in saliva at 24 weeks. EPV-608-treated boars had significantly lower tissue androstenone concentration (6.56±0.97 ng/g) compared to intact control (58.25±15.05 ng/g) boars at 26 weeks of age. In the castrated boars, back fat tissue androstenone concentration was 2.15±0.95 ng/g (FIG. 3).

Example 3—Effects of EPV-608 Treatment on Meat Quality

EPV-608 is an injectable implant, composed of PLGA (CAS #26780-50-7) as the excipient and two APIs: 100 mg TBA (CAS #10161-34-9) and 14 mg EB (CAS #50-50-0).

Treatment of animals. Neonatal male piglets (Large White X Landrace) were treated with EPV-608 on day 1 after birth. EPV-608 was injected subcutaneously in the backside of the neck (n=3). After injection, the puncture site was sealed using surgical sealant. There were two control groups; 12 piglets castrated on day 1 after birth and 21 untreated piglets (retaining testes) that remained as intact Controls. All piglets were raised in the same pen until they reach slaughter age of 26 weeks.

Slaughter and measurements. Pigs were slaughtered at 26 weeks of age. The thickness (inch) of back fat and area (cm²) of loin eye were measured to provide an estimate of meat quality. Data are presented as mean±SD. Statistical analysis was determined by One-way ANOVA.

Results

Figure 4:
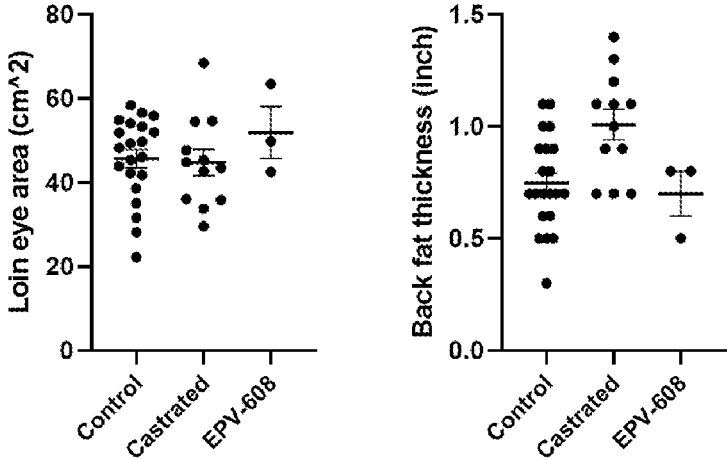
FIG. 4 illustrates exemplary pig loin eye area and back fat thickness from three subject groups (intact, castrated, EPV-608) at 26 weeks of age.

EPV-608-treated boars had better yield in meat production at 26 weeks than was seen after both castration (the industry standard husbandry procedure) and the intact control boars. In EPV-608-treated boars, the loin eye area mean was 51.92±6.16 cm², while the mean area in castrated pigs was 44.77±3.11 cm² and in the intact controls 45.68±2.16 cm² (FIG. 4). A similar beneficial response was observed for back fat thickness. In EPV-608-treated boars, back fat thickness mean was 0.70±0.10 cm², compared to 1.00±0.07 cm² in the castrated pigs and 0.75±0.05 cm² in the intact controls (FIG. 4). These data are important, because a larger loin eye area and less fatty bacon are two of several consumer preferences in pork quality (136, 137).

BIBLIOGRAPHY

1. Sutherland M A. Welfare implications of invasive piglet husbandry procedures, methods of alleviation and alternatives: a review. N Z Vet J. 2015; 63(1):52-7.
2. Rydhmer L, Zamaratskaia G, Andersson H K, Algers B, Guillemet R, Lundström K. Aggressive and sexual behaviour of growing and finishing pigs reared in groups, without castration. Acta Agriculturae Scandinavica, Section A—Animal Science. 2006; 56(2): 109-19.
3. Bonneau M, Weiler U. Pros and Cons of Alternatives to Piglet Castration: Welfare, Boar Taint, and Other Meat Quality Traits. Animals (Basel). 2019; 9(11).
4. Patterson R L S. 5α-androst-16-ene-3-one: —Compound responsible for taint in boar fat. J Sci Food Agric. 1968; 19(1):31-8.
5. Bonneau M, Kempster A J, Claus R, Claudi-Magnussen C, Diestre A, Tornberg E, et al. An international study on the importance of androstenone and skatole for boar taint: I. Presentation of the programme and measurement of boar taint compounds with different analytical procedures. Meat Sci. 2000; 54(3):251-9.
6. Aldal I, Andresen Ø, Egeli A K, Haugen J-E, Grødum A, Fjetland O, et al. Levels of androstenone and skatole and the occurrence of boar taint in fat from young boars. Livestock Production Science. 2005; 95(1): 121-9.
7. Andresen Ø. Boar taint related compounds: Androstenone/skatole/other substances. Acta Veterinaria Scandinavica. 2006; 48(1):S5.
8. Booth W D. Factors affecting the pheromone composition of voided boar saliva. J Reprod Fertil. 1987; 81(2):427-31.
9. Garcia-Regueiro J A, Diaz I. Evaluation of the contribution of skatole, indole, androstenone and androstenols to boar-taint in back fat of pigs by HPLC and capillary gas chromatography (CGC). Meat Sci. 1989; 25(4):307-16.
10. Bonneau M, Meusy-Dessolle N, Leglise P C, Claus R. Relationships between fat and plasma androstenone and plasma testosterone in fatty and lean young boars during growth and after hCG stimulation. Acta Endocrinol (Copenh). 1982; 101(1):119-28.
11. Claus R, Hoffman B, Karg H. Determination of 5-androst-16-en-3-one, a boar taint steroid in pigs, with reference to relationships to testosterone. J Anim Sci. 1971; 33(6):1293-7.
12. Zamaratskaia G, Babol J, Andersson H, Lundström K. Plasma skatole and androstenone levels in entire male pigs and relationship between boar taint compounds, sex steroids and thyroxine at various ages. Livestock Production Science. 2004; 87(2):91-8.

13. Brooks R I, Pearson A M. Steroid hormone pathways in the pig, with special emphasis on boar odor: a review. J Anim Sci. 1986; 62(3):632-45.

14. Pokorná K, Čítek J, Doležal P, Małopolska M, Tyra M, Okrouhlá M, et al. Changes of Androstenone Concentrations in Saliva of Boars with Age. Animals (Basel). 2022; 12(2).

15. Lopez-Bote C, Ventanas J. The reduction of boar taint in male pigs by neonatal testosterone administration. Meat Sci. 1988; 22(3):163-71.

16. Williamson D E, Patterson R L S. A selective immunization procedure against 5α-androstenone in boars. Animal Science. 1982; 35(3):353-60.

17. Babol J, Squires E J, Lundstrom K. Relationship between metabolism of androstenone and skatole in intact male pigs. J Anim Sci. 1999; 77(1):84-92.

18. Doran E, Whittington F W, Wood J D, McGivan J D. Cytochrome P450IIE1 (CYP2E1) is induced by skatole and this induction is blocked by androstenone in isolated pig hepatocytes. Chem Biol Interact. 2002; 140(1):81-92.

19. Grindflek E, Meuwissen T H, Aasmundstad T, Hamland H, Hansen M H, Nome T, et al. Revealing genetic relationships between compounds affecting boar taint and reproduction in pigs. J Anim Sci. 2011; 89(3):680-92.

20. Zamaratskaia G, Gilmore W J, Lundstrom K, Squires E J. Effect of testicular steroids on catalytic activities of cytochrome P450 enzymes in porcine liver microsomes. Food Chem Toxicol. 2007; 45(4):676-81.

21. Rasmussen M K, Zamaratskaia G. Regulation of porcine hepatic cytochrome p450—implication for boar taint. Comput Struct Biotechnol J. 2014; 11(19):106-12.

22. Kaufmann G, Ritter F, Schubert K. Quantitative determination of the boar taint substance 5alpha-androst-16-en-3-one in fat. J Steroid Biochem. 1976; 7:593-7.

23. Lervik S, Oskam I, Krogenaes A, Andresen O, Dahl E, Haga H A, et al. Androstenone and testosterone levels and testicular morphology of Duroc boars related to estimated breeding value for androstenone. Theriogenology. 2013; 79(6):986-94.

24. Batrinos M L. Testosterone and aggressive behavior in man. Int J Endocrinol Metab. 2012; 10(3):563-8.

25. Giersing M, Lundstrom K, Andersson A. Social effects and boar taint: significance for production of slaughter boars (Sus scrofa). J Anim Sci. 2000; 78(2):296-305.

26. Parois S P, Faouen A, Le Floc'h N, Prunier A. Influence of the inflammatory status of entire male pigs on their pubertal development and fat androstenone. Animal. 2017; 11(6):1071-7.

27. Griffiths N M, Patterson R L. Human olfactory responses to 5-alpha-androst-16-en-3-one—principal component of boar taint. J Sci Food Agric. 1970; 21(1):4-6.

28. Bonneau M, Walstra P, Claudi-Magnussen C, Kempster A J, Tornberg E, Fischer K, et al. An international study on the importance of androstenone and skatole for boar taint: IV. Simulation studies on consumer dissatisfaction with entire male pork and the effect of sorting carcasses on the slaughter line, main conclusions and recommendations. Meat Sci. 2000; 54(3):285-95.

29. Čandek-Potokar M, Batorek-Lukac N. Alternatives to surgical castration of pigs. Životnov Dni Nauki. 2015; 52(5):41-51.

30. Lunstra D D, Ford J J, Christenson R K, Allrich R D. Changes in Leydig cell ultrastructure and function during pubertal development in the boar. Biology of reproduction. 1986; 34(1):145-58.

31. Allrich R D, Christenson R K, Ford J J, Zimmerman D R. Pubertal development of the boar: age-related changes in testicular morphology and in vitro production of testosterone and estradiol-17 beta. Biology of reproduction. 1983; 28(4):902-9.

32. Raeside J I, Renaud R L. Estrogen and androgen production by purified Leydig cells of mature boars. Biology of reproduction. 1983; 28(3):727-33.

33. von Borell E, Baumgartner J, Giersing M, Jäggin N, Prunier A, Tuyttens F, et al. Animal welfare implications of surgical castration and its alternatives in pigs. Animal: an international journal of animal bioscience. 2009; 3:1488-96.

34. Garcia A. Towards an improved method of piglet castration to reduce pain: the use of one incision in combination with the use of a Vapocoolant and Metacam™ (C-17-037). Des Moines, IA: National Port Board; 2019.

35. Rault J-L, Lay D, Marchant-Forde J. Castration induced pain in pigs and other livestock. Appl Anim Behav Sci. 2011; 135.

36. Viscardi A V, Turner P V. Use of Meloxicam or Ketoprofen for Piglet Pain Control Following Surgical Castration. Front Vet Sci. 2018; 5:299.

37. Cronin G M, Dunshea F R, Butler K L, McCauley I, Barnett J L, Hemsworth P H. The effects of immuno- and surgical-castration on the behaviour and consequently growth of group-housed, male finisher pigs. Applied Animal Behaviour Science. 2003; 81(2):111-26.

38. Tomikawa J, Homma T, Tajima S, Shibata T, Inamoto Y, Takase K, et al. Molecular characterization and estrogen regulation of hypothalamic KISS1 gene in the pig. Biology of reproduction. 2010; 82(2):313-9.

39. Scott C J, Rose J L, Gunn A J, McGrath B M. Kisspeptin and the regulation of the reproductive axis in domestic animals. J Endocrinol. 2019; 240:R1-R16.

40. Yeo S H, Colledge W H. The Role of Kiss1 Neurons As Integrators of Endocrine, Metabolic, and Environmental Factors in the Hypothalamic-Pituitary-Gonadal Axis. Front Endocrinol (Lausanne). 2018; 9:188.

41. Yeo S H, Kyle V, Blouet C, Jones S, Colledge W H. Mapping neuronal inputs to Kiss1 neurons in the arcuate nucleus of the mouse. PLOS One. 2019; 14(3):e0213927.

42. Novaira H J, Sonko M L, Hoffman G, Koo Y, Ko C, Wolfe A, et al. Disrupted kisspeptin signaling in GnRH neurons leads to hypogonadotrophic hypogonadism. Mol Endocrinol. 2014; 28(2):225-38.

43. d'Anglemont de Tassigny X, Fagg L A, Dixon J P, Day K, Leitch H G, Hendrick A G, et al. Hypogonadotropic hypogonadism in mice lacking a functional Kiss1 gene. Proceedings of the National Academy of Sciences of the United States of America. 2007; 104(25): 10714-9.

44. Cortes M E, Carrera B, Rioseco H, Pablo del Rio J, Vigil P. The Role of Kisspeptin in the Onset of Puberty and in the Ovulatory Mechanism: A Mini-review. J Pediatr Adolesc Gynecol. 2015; 28(5):286-91.

45. Terasawa E, Guerriero K A, Plant T M. Kisspeptin and puberty in mammals. Adv Exp Med Biol. 2013; 784:253-73.

46. Uenoyama Y, Inoue N, Nakamura S, Tsukamura H. Central Mechanism Controlling Pubertal Onset in Mammals: A Triggering Role of Kisspeptin. Front Endocrinol (Lausanne). 2019; 10:312.

47. Seminara S B, Messager S, Chatzidaki E E, Thresher R R, Acierno J S, Jr., Shagoury J K, et al. The GPR54 gene as a regulator of puberty. N Engl J Med. 2003; 349(17): 1614-27.

48. Messager S, Chatzidaki E E, Ma D, Hendrick A G, Zahn D, Dixon J, et al. Kisspeptin directly stimulates gonadotropin-releasing hormone release via G protein-coupled receptor 54. Proc Natl Acad Sci USA. 2005; 102(5):1761-6.

49. Funes S, Hedrick J A, Vassileva G, Markowitz L, Abbondanzo S, Golovko A, et al. The KiSS-1 receptor GPR54 is essential for the development of the murine reproductive system. Biochem Biophys Res Commun. 2003; 312(4):1357-63.

50. Ikegami K, Goto T, Nakamura S, Watanabe Y, Sugimoto A, Majarune S, et al. Conditional kisspeptin neuron-specific Kiss1 knockout with newly generated Kiss1-floxed and Kiss1-Cre mice replicates a hypogonadal phenotype of global Kiss1 knockout mice. J Reprod Dev. 2020; 66(4):359-67.

51. Lapatto R, Pallais J C, Zhang D, Chan Y M, Mahan A, Cerrato F, et al. Kiss1−/− mice exhibit more variable hypogonadism than Gpr54−/− mice. Endocrinology. 2007; 148(10):4927-36.

52. Minabe S, Nakamura S, Fukushima E, Sato M, Ikegami K, Goto T, et al. Inducible Kiss1 knockdown in the hypothalamic arcuate nucleus suppressed pulsatile secretion of luteinizing hormone in male mice. J Reprod Dev. 2020.

53. Chen J, Minabe S, Munetomo A, Magata F, Sato M, Nakamura S, et al. Kiss1-dependent and independent release of luteinizing hormone and testosterone in perinatal male rats. Endocr J. 2022.

54. Minabe S, Sato M, Inoue N, Watanabe Y, Magata F, Matsuda F, et al. Neonatal Estrogen Causes Irreversible Male Infertility via Specific Suppressive Action on Hypothalamic Kiss1 Neurons. Endocrinology. 2019; 160(5): 1223-33.

55. Gettys T W, D'Occhio M J, Henricks D M, Schanbacher B D. Suppression of LH secretion by oestradiol, dihydrotestosterone and trenbolone acetate in the acutely castrated bull. J Endocrinol. 1984; 100(1): 107-12.

56. Schanbacher B D, Johnson M P, Tindall D J. Androgenic regulation of luteinizing hormone secretion: relationship to androgen binding in sheep pituitary. Biology of reproduction. 1987; 36(2):340-50.

57. Bateman H L, Patisaul H B. Disrupted female reproductive physiology following neonatal exposure to phytoestrogens or estrogen specific ligands is associated with decreased GnRH activation and kisspeptin fiber density in the hypothalamus. Neurotoxicology. 2008; 29(6):988-97.

58. Minabe S, Ieda N, Watanabe Y, Inoue N, Uenoyama Y, Maeda K I, et al. Long-Term Neonatal Estrogen Exposure Causes Irreversible Inhibition of LH Pulses by Suppressing Arcuate Kisspeptin Expression via Estrogen Receptors alpha and beta in Female Rodents. Endocrinology. 2017; 158(9):2918-29.

59. Berger T, Conley A J, Van Klompenberg M, Roser J F, Hovey R C. Increased testicular Sertoli cell population induced by an estrogen receptor antagonist. Mol Cell Endocrinol. 2013; 366(1):53-8.

60. Berger T, Nitta-Oda B J. Increased testicular estradiol during the neonatal interval reduces Sertoli cell numbers. Anim Reprod Sci. 2018; 189:146-51.

61. Kao E, Villalon R, Ribeiro S, Berger T. Role for endogenous estrogen in prepubertal Sertoli cell maturation. Anim Reprod Sci. 2012; 135(1-4):106-12.

62. Berger T, Kentfield L M, Roser J F, Conley A J. Stimulation of Sertoli Cell Proliferation: Defining the Response Interval to an Inhibitor of Estrogen Synthesis in the Boar. Reproduction. 2012; 143(4):523-9.

63. Berger T, McCarthy M, Pearl C A, At-Taras E, Roser J F, Conley A. Reducing endogenous estrogens during the neonatal and juvenile periods affects reproductive tract development and sperm production in postpuberal boars. Anim Reprod Sci. 2008; 109(1-4):218-35.

64. Van Straaten H W, Wensing C J. Leydig cell development in the testis of the pig. Biol Reprod. 1978; 18(1): 86-93.

65. Hess R A. Small tubules, surprising discoveries: from efferent ductules in the turkey to the discovery that estrogen receptor alpha is essential for fertility in the male. Anim Reprod. 2015; 12(1):7-23.

66. Lara N L M, Costa G M J, Avelar G F, Lacerda S M S N, Hess R A, de França L R. Testis Physiology—Overview and Histology. In: Skinner M K, editor. Encyclopedia of Reproduction (Second Edition). 1. San Diego: Academic Press: Elsevier; 2018. p. 105-16.

67. Lara N L M, Avelar G F, Costa G M J, Lacerda S M S N, Hess R A, de França L R. Cell-Cell Interactions-Structural. In: Skinner M K, editor. Encyclopedia of Reproduction (Second Edition). 1. Oxford: Academic Press; 2018. p. 68-75.

68. Bonneau M, Carrié-Lemoine J, Prunier A, Garnier D H, Terqui M. Age-related changes in plasma LH and testosterone concentration profiles and fat 5α-androstenone content in the young boar. Animal Reproduction Science. 1987; 15(3):241-58.

69. Bonneau M. Effects of age and live weight on fat 5 alpha-androstenone levels in young boars fed two planes of nutrition. Reproduction, nutrition, development. 1987; 27(2a):413-22.

70. Bonneau M. Compounds responsible for boar taint, with special emphasis on androstenone: A review. Livestock Production Science. 1982; 9(6):687-705.

71. Claus R, Hoffmann B. Oestrogens, compared to other steroids of testicular origin, in blood plasma of boars. Acta Endocrinol (Copenh). 1980; 94(3):404-11.

72. Rebourcet D, Darbey A, Monteiro A, Soffientini U, Tsai Y T, Handel I, et al. Sertoli Cell Number Defines and Predicts Germ and Leydig Cell Population Sizes in the Adult Mouse Testis. Endocrinology. 2017; 158(9):2955-69.

73. Chen M, Wang X, Wang Y, Zhang L, Xu B, Lv L, et al. Wt1 is involved in leydig cell steroid hormone biosynthesis by regulating paracrine factor expression in mice. Biology of reproduction. 2014; 90(4).

74. Rebourcet D, O'Shaughnessy P J, Pitetti J L, Monteiro A, O'Hara L, Milne L, et al. Sertoli cells control peritubular myoid cell fate and support adult Leydig cell development in the prepubertal testis. Development. 2014; 141(10):2139-49.

75. De Gendt K, Atanassova N, Tan K A, de Franca L R, Parreira G G, McKinnell C, et al. Development and function of the adult generation of Leydig cells in mice with Sertoli cell-selective or total ablation of the androgen receptor. Endocrinology. 2005; 146(9):4117-26.

76. Kothandapani A, Larsen M C, Lee J, Jorgensen J S, Jefcoate C R. Distinctive functioning of STARD1 in the fetal Leydig cells compared to adult Leydig and adrenal cells. Impact of Hedgehog signaling via the primary cilium. Mol Cell Endocrinol. 2021; 531:111265.

77. Trudeau V L, Meijer J C, Erkens J H, van de Wiel D F, Wensing C J. Pubertal development in the male pig: effects of treatment with a long-acting gonadotropin-releasing hormone agonist on plasma luteinizing hormone, follicle stimulating hormone and testosterone. Can J Vet Res. 1992; 56(2):102-9.

78. Colenbrander B, Kruip T A, Dieleman S J, Wensing C J. Changes in serum LH concentrations during normal and abnormal sexual development in the pig. Biology of reproduction. 1977; 17(4):506-13.

79. van Straaten H W. Lack of primary defect in maldescended testis of the neonatal pig. Biology of reproduction. 1978; 19(5):994-8.

80. Picut C A, Remick A K, de Rijk E P, Simons M L, Stump D G, Parker G A. Postnatal development of the testis in the rat: morphologic study and correlation of morphology to neuroendocrine parameters. Toxicol Pathol. 2015; 43(3):326-42.

81. Shima Y. Development of fetal and adult Leydig cells. Reprod Med Biol. 2019; 18(4):323-30.

82. Rebourcet D, Monteiro A, Cruickshanks L, Jeffery N, Smith S, Milne L, et al. Relationship of transcriptional markers to Leydig cell number in the mouse testis. PLOS ONE. 2019; 14(7):e0219524.

83. Ford J J. Serum estrogen concentrations during postnatal development in male pigs. Proc Soc Exp Biol Med. 1983; 174(2): 160-4.

84. Berger T, Conley A. Reduced Endogenous Estrogen and Hemicastration Interact Synergistically to Increase Porcine Sertoli Cell Proliferation1. Biology of reproduction. 2014; 90(5).

85. Berger T, Conley A J. Reducing endogenous estrogen during prepuberal life does not affect boar libido or sperm fertilizing potential. Theriogenology. 2014; 82(4):627-35.

86. Wagner A, Claus R. Aromatase and 11beta-hydroxysteroid dehydrogenase 2 localisation in the testes of pigs from birth to puberty linked to changes of hormone pattern and testicular morphology. Reprod Fertil Dev. 2008; 20(4):505-12.

87. Kangawa A, Otake M, Enya S, Yoshida T, Shibata M. Histological Changes of the Testicular Interstitium during Postnatal Development in Microminipigs. Toxicologic pathology. 2019; 47(4):469-82.

88. Ramesh R, Pearl C A, At-Taras E, Roser J F, Berger T. Ontogeny of androgen and estrogen receptor expression in porcine testis: effect of reducing testicular estrogen synthesis. Anim Reprod Sci. 2007; 102(3-4):286-99.

89. Crépieux P, Marion S, Martinat N, Fafeur V, Vern Y L, Kerboeuf D, et al. The ERK-dependent signalling is stage-specifically modulated by FSH, during primary Sertoli cell maturation. Oncogene. 2001; 20(34):4696-709.

90. Wells R, Kenny A L, Duckett R, Wreford N G, Johnston S D, D'Occhio M J. Elucidation of the role of LH and FSH during neonatal testicular development and growth in the boar. Animal reproduction science. 2013; 137(1-2):74-81.

91. Saez J M, Sanchez P, Berthelon M C, Avallet O. Regulation of pig Leydig cell aromatase activity by gonadotropins and Sertoli cells. Biol Reprod. 1989; 41(5): 813-20.

92. Oduwole O O, Huhtaniemi I T, Misrahi M. The Roles of Luteinizing Hormone, Follicle-Stimulating Hormone and Testosterone in Spermatogenesis and Folliculogenesis Revisited. Int J Mol Sci. 2021; 22(23).

93. Ramaswamy S, Weinbauer G F. Endocrine control of spermatogenesis: Role of FSH and LH/testosterone. Spermatogenesis. 2014; 4(2):e996025.

94. Mruk D D, Cheng C Y. Sertoli-Sertoli and Sertoli-germ cell interactions and their significance in germ cell movement in the seminiferous epithelium during spermatogenesis. Endocr Rev. 2004; 25(5):747-806.

95. Meroni S B, Galardo M N, Rindone G, Gorga A, Riera M F, Cigorraga S B. Molecular Mechanisms and Signaling Pathways Involved in Sertoli Cell Proliferation. Front Endocrinol (Lausanne). 2019; 10:224.

96. Rebourcet D, O'Shaughnessy P J, Monteiro A, Milne L, Cruickshanks L, Jeffrey N, et al. Sertoli cells maintain Leydig cell number and peritubular myoid cell activity in the adult mouse testis. PLOS One. 2014; 9(8):e105687.

97. Legacki E, Conley A J, Nitta-Oda B J, Berger T. Porcine sertoli cell proliferation after androgen receptor inactivation. Biology of reproduction. 2015; 92(4):93.

98. Mendis-Handagama S M, Ariyaratne H B. Differentiation of the adult Leydig cell population in the postnatal testis. Biol Reprod. 2001; 65(3):660-71.

99. Tousson E, El-Moghazy M, Massoud A, Akel A. Histopathological and Immunohistochemical Changes in the Testes of Rabbits After Injection With the Growth Promoter Boldenone. Reproductive Sciences. 2012; 19(3): 253-9.

100. Singh J, Handelsman D J. Neonatal administration of FSH increases Sertoli cell numbers and spermatogenesis in gonadotropin-deficient (hpg) mice. J Endocrinol. 1996; 151(1):37-48.

101. Allan C M, Garcia A, Spaliviero J, Zhang F P, Jimenez M, Huhtaniemi I, et al. Complete Sertoli cell proliferation induced by follicle-stimulating hormone (FSH) independently of luteinizing hormone activity: evidence from genetic models of isolated FSH action. Endocrinology. 2004; 145(4): 1587-93.

102. At-Taras E E, Berger T, McCarthy M J, Conley A J, Nitta-Oda B J, Roser J F. Reducing estrogen synthesis in developing boars increases testis size and total sperm production. J Androl. 2006; 27(4):552-9.

103. Lunstra D D, Ford J J, Klindt J, Wise T H. Physiology of the Meishan boar. J Reprod Fertil Suppl. 1997; 52:181-93.

104. McCoard S A, Wise T H, Lunstra D D, Ford J J. Stereological evaluation of Sertoli cell ontogeny during fetal and neonatal life in two diverse breeds of swine. J Endocrinol. 2003; 178(3):395-403.

105. Ford J J, McCoard S A, Wise T H, Lunstra D D, Rohrer G A. Genetic variation in sperm production. Soc Reprod Fertil Suppl. 2006; 62:99-112.

106. Lunstra D D, Wise T H, Ford J J. Sertoli cells in the boar testis: changes during development and compensatory hypertrophy after hemicastration at different ages. Biol Reprod. 2003; 68(1):140-50.

107. Swanlund D J, N'Diaye M R, Loseth K J, Pryor J L, Crabo B G. Diverse testicular responses to exogenous growth hormone and follicle-stimulating hormone in prepubertal boars. Biology of reproduction. 1995; 53(4):749-57.

108. Hess R A, Sharpe R M, Hinton B T. Estrogens and development of the rete testis, efferent ductules, epididymis and vas deferens. Differentiation. 2021:(in press).

109. Atanassova N, McKinnell C, Walker M, Turner K J, Fisher J S, Morley M, et al. Permanent effects of neonatal estrogen exposure in rats on reproductive hormone levels, Sertoli cell number, and the efficiency of spermatogenesis in adulthood. Endocrinology. 1999; 140(11):5364-73.

110. Vandalem J L, McNamara M, Petit R, Hennen G. Developmental changes in gonadotrophins and testicular gonadotrophin receptors in the pig, from neonatal to adult life. Journal of Endocrinology. 1986; 111(2):301-8.

111. Kosco M S, Loseth K J, Crabo B G. Development of the seminiferous tubules after neonatal hemicastration in the boar. J Reprod Fertil. 1989; 87(1):1-11.

112. Tran D, Meusy-Dessolle N, Josso N. Waning of anti-mullerian activity: an early sign of sertoli cell maturation in the developing pig. Biol Reprod. 1981; 24(4):923-31.

113. Srisuwatanasagul K, Srisuwatanasagul S, Roongsitthichai A. Expressions of cytochrome P450 aromatase and anti-Müllerian hormone in testes of fattening pigs by the timing of the first vaccination for immunocastration. Reproduction in Domestic Animals. 2021; n/a (n/a).

114. Geiger T L, Khan M, Whisnanta C S, Prien S D, Khanc S A. Regulation of DNA synthesis in leydig cells obtained from neonatal pig testes. Domestic Animal Endocrinology. 1999; 17(1):65-75.

115. Franca L R, Silva V A, Jr., Chiarini-Garcia H, Garcia S K, Debeljuk L. Cell proliferation and hormonal changes during postnatal development of the testis in the pig. Biology of reproduction. 2000; 63(6):1629-36.

116. Schwarzenberger F, Toole G S, Christie H L, Raeside J I. Plasma levels of several androgens and estrogens from birth to puberty in male domestic pigs. Acta Endocrinol (Copenh). 1993; 128(2):173-7.

117. Colenbrander B, de Jong F H, Wensing C J. Changes in serum testosterone concentrations in the male pig during development. J Reprod Fertil. 1978; 53(2):377-80.

118. Daxenberger A, Hageleit M, Kraetzl W-D, Lange I G, Claus R, Le Bizec B, et al. Suppression of androstenone in entire male pigs by anabolic preparations. Livestock Production Science. 2001; 69(2): 139-44.

119. Sheridan P J, Austin F H, Bourke S, Roche J F. The effect of anabolic agents on growth rate and reproductive organs of pigs. Livestock Production Science. 1990; 26(4):263-75.

120. López-Bote C, Sancho G, Martínez M, Ventanas J, Gázquez A, Roncero V. Trenbolone Acetate Induced Changes in the Genital Tract of Male Pigs. Journal of Veterinary Medicine, Series B. 1994; 41(1-10):42-8.

121. Ventanas J, Sancho G, Garcia-Regueiro J A, Antequera T, Martinez M, López-Bote C. Testicular development, androstenone levels and androstenone odour of untreated and trenbolone implanted boars. Journal of the Science of Food and Agriculture. 1991; 57(1): 127-33.

122. van Vorstenbosch C J, Colenbrander B, Wensing C J. Leydig cell development in the pig testis during the late fetal and early postnatal period: an electron microscopic study with attention to the influence of fetal decapitation. Am J Anat. 1984; 169(2):121-36.

123. Robic A, Feve K, Louveau I, Riquet J, Prunier A. Exploration of steroidogenesis-related genes in testes, ovaries, adrenals, liver and adipose tissue in pigs. Anim Sci J. 2016; 87(8):1041-7.

124. Robic A, Feve K, Riquet J, Prunier A. Transcript levels of genes implicated in steroidogenesis in the testes and fat tissue in relation to androstenone accumulation in fat of pubertal pigs. Domest Anim Endocrinol. 2016; 57:1-9.

125. Ye L, Li X, Li L, Chen H, Ge R S. Insights into the Development of the Adult Leydig Cell Lineage from Stem Leydig Cells. Front Physiol. 2017; 8:430.

126. Ventanas J, López-Bote C J, García C. Further signs of postnatal sexual differentiation in pigs. Exp Clin Endocrinol. 1992; 99(3): 119-22.

127. Corbin C J, Berger T, Ford J J, Roselli C E, Sienkiewicz W, Trainor B C, et al. Porcine hypothalamic aromatase cytochrome P450: isoform characterization, sex-dependent activity, regional expression, and regulation by enzyme inhibition in neonatal boars. Biology of reproduction. 2009; 81(2):388-95.

128. Naftolin F, Ryan K J, Davies I J, Reddy V V, Flores F, Petro Z, et al. The formation of estrogens by central neuroendocrine tissues. Recent Prog Horm Res. 1975; 31:295-319.

129. Haeussler S, Wagner A, Welter H, Claus R. Changes of testicular aromatase expression during fetal development in male pigs (Sus scrofa). Reproduction. 2007; 133(1): 323-30.

130. Sidman K R, Steber W D, Schwope A D, Schnaper G R. Controlled release of macromolecules and pharmaceuticals from synthetic polypeptides based on glutamic acid. Biopolymers. 1983; 22(1):547-56.

131. Langer R, Brem H, Tapper D. Biocompatibility of polymeric delivery systems for macromolecules. J Biomed Mater Res. 1981; 15(2):267-77.

132. Langer R. Controlled release of macromolecules. 1982.

133. Eppstein D A, Marsh Y V, van der Pas M, Felgner P L, Schreiber A B. Biological activity of liposome-encapsulated murine interferon gamma is mediated by a cell membrane receptor. Proc Natl Acad Sci USA. 1985; 82(11):3688-92.

134. Bonneau M B, Denmat Ml, Vaudelet J C, Nunes J R V, Mortensen A B, Mortensen H P. Contributions of fat androstenone and skatole to boar taint: II. Eating quality of cooked hams. Livestock Production Science. 1992; 32:81-8.

135. Bone C, Squires E J. The Uptake and Deconjugation of Androstenone Sulfate in the Adipose Tissue of the Boar. Animals (Basel). 2021; 11(11).

136. Lee Y E, Lee H J, Kim M, Yoon J W, Ryu M, Jo C. Analysis on difference of consumer's evaluation on visual features of pork cuts. J Anim Sci Technol. 2021; 63(3): 614-25.

137. McLean K G, Hanson D J, Jervis S M, Drake M A. Consumer Perception of Retail Pork Bacon Attributes Using Adaptive Choice-based Conjoint Analysis and Maximum Differential Scaling. J Food Sci. 2017; 82(11): 2659-68.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof) or with respect to other examples (or one or more aspects thereof) shown or described herein.

In the event of inconsistent usages between this document and any documents so incorporated by reference, the usage in this document controls.

The above description is intended to be illustrative and not restrictive. For example, the above-described examples (or one or more aspects thereof) may be used in combination with each other. Other embodiments can be used, such as by one of ordinary skill in the art" upon reviewing the above description. The Abstract is provided to comply with 37 C.F.R. § 1.72(b) to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in fewer than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims along with the full scope of equivalents to which such claims are entitled.

Several Embodiments

1. A method for inhibiting testicular development in the pig, which prevents the pubertal rise in blood and tissue androgens comprising injecting in said pig a combination of an estrogen and an androgen neonatally.

2. The method of statement 1, wherein the injection is either subcutaneous or intramuscular.

3. The method of statement 1 or 2, further comprising an implant wherein the implant comprises said estrogen and androgen.

4. The method of any one of statements 1 to 3, wherein the estrogen and androgen target hypothalamus-pituitary axis and testis development, respectively.

5. The method of any one of statements 1 to 4, wherein the implant comprises a material or enclosure that provides sustained release of the compounds over nursery period.

6. The method of any one of statements 1 to 5, wherein the injected estrogen and androgen are not present in the blood or tissues when the pigs are slaughtered.

7. The method of statement 5 or 6, wherein the material or enclosure that provides sustained release consists with biodegradable polymers or biocompatible materials.

8. The method of statement 7, wherein the material or enclosure that provides sustained release is a capsule, pellet, microsphere, gel, or solution form.

9. The method of any one of statements 1 to 8, wherein the estrogen comprises one or more estradiol esters at dose range of about 1-40 mg per pig.

10. The method of any one of statements 1 to 9, wherein the androgen comprises trenbolone, trenbolone acetate, 5α-dihydrotestostrone, 5α-dihydrotestostrone acetate or equivalents with a dose range of about 25-200 mg per pig.

11. The method of any one of statements 1 to 10, wherein the injected amount of the estrogen/androgen combination is in a dose sufficient to inhibit kisspeptin neurons in the hypothalamus, LH production in the pituitary, Sertoli cell proliferation in the testis and/or Leydig cell proliferation and production of androstenone in the testis and androstenone accumulation in the fat.

All publications, patents, and patent applications, Genbank sequences, websites and other published materials referred to throughout the disclosure herein are herein incorporated by reference to the same extent as if each individual publication, patent, or patent application, Genbank sequences, websites and other published materials was specifically and individually indicated to be incorporated by reference. In the event that the definition of a term incorporated by reference conflicts with a term defined herein, this specification shall control.

What is claimed is:

1. A method to inhibit boar taint in a pig comprising injecting in said pig a combination of an estrogen and an androgen neonatally in a dose sufficient to inhibit said boar taint until the pig is slaughtered, wherein the estrogen and androgen are in an implant, wherein the dose is sufficient to inhibit androstenone accumulation in fat which prevents boar taint development in cooked pork.

2. The method of claim 1, wherein the boar taint is inhibited for 24 to 26 weeks of age.

3. The method of claim 1, wherein in the injection is subcutaneous or intra-muscular.

4. The method of claim 1, wherein the implant comprises a material or enclosure that provides sustained release of the compounds over nursery period.

5. The method of claim 4, wherein the material or enclosure that provides sustained release comprises biodegradable polymers or biocompatible materials.

6. The method of claim 4, the material or enclosure that provides sustained release is a capsule, pellet, microsphere, gel or solution form.

7. The method of claim 1, wherein the estrogen comprises one or more estradiol esters at a dosage range of about 1-40 mg per pig.

8. The method of claim 1, wherein the androgen comprises testosterone, testosterone esters, testosterone metabolites or their esters, trenbolone or trenbolone esters, or equivalents that have potent androgen activity at a dosage range of about 25-200 mg per pig.

9. The method of claim 8 wherein the testosterone metabolite is 5a-dihydrotestosterone.

10. The method of claim 8, wherein the trenbolone ester is trenbolone acetate.

11. The method of claim 1, wherein the dose is sufficient to inhibit kisspeptin neurons in hypothalamus, LH production in pituitary, Sertoli cell proliferation in testis and Leydig cell proliferation and production of androstenone in testis.

12. The method of claim 1, wherein the dose is sufficient to inhibit endogenous androgen production.

13. The method of claim 12, wherein the endogenous androgen comprises steroid hormones produced in testis.

14. The method of claim 13, wherein the steroid hormones produced in the testis comprises testosterone and androstenone.

15. The method of claim 1, wherein the dose is a single, one-time dose.

16. A method to inhibit aggression in a male pig comprising injecting in said pig a combination of an estrogen and an androgen neonatally in a dose sufficient to inhibit said aggression until the pig is slaughtered, wherein the estrogen and androgen are in an implant.

17. A method to improve the ratio of loin eye area and fat thickness in a pig comprising injecting in said pig a combination of an estrogen and an androgen neonatally in a dose sufficient to improve the ratio of loin eye area and fat thickness in the pig when the pigs are slaughtered, wherein the estrogen and androgen are in an implant.

18. A method to improve the yield in meat production in a pig comprising injecting in said pig a combination of an estrogen and an androgen neonatally in a dose sufficient to improve the yield in meat production when the pig is slaughtered as compared to a castrated pig, wherein the estrogen and androgen are in an implant.

19. The method of claim 18, wherein the improved yield in meat production comprises increased loin eye area and decreased backfat thickness.

* * * * *